(12) United States Patent
Donegan et al.

(10) Patent No.: US 12,257,399 B2
(45) Date of Patent: *Mar. 25, 2025

(54) MEDICAL CATHETER

(71) Applicant: Medtronic Vascular, Inc., Santa Rosa, CA (US)

(72) Inventors: Mick Donegan, Galway (IE); Kevin Ryan, Galway (IE); Colm Connolly, Galway (IE); Barry O'Connell, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/406,561

(22) Filed: Jan. 8, 2024

(65) Prior Publication Data

US 2024/0139472 A1    May 2, 2024

Related U.S. Application Data

(63) Continuation of application No. 16/432,763, filed on Jun. 5, 2019, now Pat. No. 11,911,573.
(Continued)

(51) Int. Cl.
| | |
|---|---|
| *A61M 25/01* | (2006.01) |
| *A61L 29/04* | (2006.01) |
| *A61M 25/00* | (2006.01) |

(52) U.S. Cl.
CPC ....... *A61M 25/0105* (2013.01); *A61L 29/049* (2013.01); *A61M 25/0045* (2013.01);
(Continued)

(58) Field of Classification Search
CPC ...... A61N 25/0068; A61M 2025/0004; A61M 25/0105; A61M 25/0045; A61M 2025/0008; A61M 25/0108; A61L 29/049
See application file for complete search history.

(56) References Cited

U.S. PATENT DOCUMENTS

| | | |
|---|---|---|
| 3,169,527 A | 2/1965 | Sheridan |
| 4,863,442 A | 9/1989 | DeMello et al. |
| | (Continued) | |

FOREIGN PATENT DOCUMENTS

| | | |
|---|---|---|
| CN | 102510763 A | 6/2012 |
| CN | 104902950 A | 9/2015 |
| | (Continued) | |

OTHER PUBLICATIONS

First Office Action and Search Report, and translation thereof, from counterpart Chinese Application No. 201980037946.6, dated May 6, 2022, 18 pp.
(Continued)

*Primary Examiner* — Darwin P Erezo
*Assistant Examiner* — Christina C Lauer
(74) *Attorney, Agent, or Firm* — Shumaker & Sieffert, P.A.

(57) ABSTRACT

A catheter may include an elongate body including a proximal portion including a proximal end, and a distal tip portion. The distal tip portion may include an inner liner and a marker band circumferentially surrounding the inner liner. The distal tip portion also may include an outer jacket circumferentially surrounding a first portion of the inner liner and ending proximal of a proximal end of the marker band; and a tip outer jacket circumferentially surrounding a second portion of the inner liner and the marker band. The tip outer jacket extends distally past the marker band distal end to a distal tip of the elongate body, and a proximal end of the tip outer jacket may be laterally adjacent to a distal end of the outer jacket.

20 Claims, 22 Drawing Sheets

Related U.S. Application Data

(60) Provisional application No. 62/848,926, filed on May 16, 2019, provisional application No. 62/680,792, filed on Jun. 5, 2018.

(52) U.S. Cl.
CPC . *A61M 25/0068* (2013.01); *A61M 2025/0004* (2013.01); *A61M 2025/0008* (2013.01); *A61M 2025/0166* (2013.01)

(56) References Cited

U.S. PATENT DOCUMENTS

| | | | |
|---|---|---|---|
| 5,188,605 A | 2/1993 | Sleep | |
| 5,387,193 A | 2/1995 | Miraki | |
| 5,403,292 A | 4/1995 | Ju | |
| 5,527,292 A | 6/1996 | Adams et al. | |
| 5,571,087 A | 11/1996 | Ressemann et al. | |
| 6,090,099 A | 7/2000 | Samson et al. | |
| 6,368,316 B1 | 4/2002 | Jansen et al. | |
| 6,652,507 B2 | 11/2003 | Pepin | |
| 6,761,696 B1 | 7/2004 | Wong | |
| 7,419,501 B2 | 9/2008 | Chiu et al. | |
| 7,736,355 B2 | 6/2010 | Itou et al. | |
| 8,133,267 B2 | 3/2012 | Leonhardt et al. | |
| 8,328,759 B2 | 12/2012 | Donawick | |
| 9,023,096 B2 | 5/2015 | Dwork | |
| 9,352,123 B2 | 5/2016 | Zhou et al. | |
| 9,675,486 B2 | 6/2017 | Jimenez, Jr. et al. | |
| 11,541,208 B2 | 1/2023 | Mcevoy et al. | |
| 11,559,663 B2 | 1/2023 | Hannon et al. | |
| 11,911,573 B2 * | 2/2024 | Donegan | A61M 25/0068 |
| 2002/0022825 A1 | 2/2002 | Saitou et al. | |
| 2002/0161395 A1 | 10/2002 | Douk et al. | |
| 2003/0009150 A1 | 1/2003 | Pepin | |
| 2003/0125641 A1 | 7/2003 | Jafari et al. | |
| 2003/0208221 A1 | 11/2003 | El-Nounou | |
| 2004/0087932 A1 | 5/2004 | Lawrence et al. | |
| 2004/0122360 A1 | 6/2004 | Waldhauser et al. | |
| 2005/0054952 A1 | 3/2005 | Eskuri et al. | |
| 2005/0065498 A1 | 3/2005 | McFerran | |
| 2005/0148866 A1 | 7/2005 | Gunderson | |
| 2008/0051808 A1 | 2/2008 | Rivera et al. | |
| 2008/0243081 A1 | 10/2008 | Nance et al. | |
| 2009/0030400 A1 | 1/2009 | Bose et al. | |
| 2009/0264865 A1 | 10/2009 | Kawai | |
| 2010/0022264 A1 | 1/2010 | Kwon et al. | |
| 2010/0121269 A1 * | 5/2010 | Goldenberg | A61M 25/0105 604/95.01 |
| 2010/0217234 A1 | 8/2010 | Grovender et al. | |
| 2010/0222664 A1 | 9/2010 | Lemon et al. | |
| 2012/0136340 A1 | 5/2012 | Tanioka | |
| 2013/0237962 A1 | 9/2013 | Kawai | |
| 2014/0005647 A1 | 1/2014 | Shuffler et al. | |
| 2014/0012281 A1 | 1/2014 | Wang et al. | |
| 2014/0039461 A1 | 2/2014 | Anderson et al. | |
| 2014/0052097 A1 | 2/2014 | Petersen et al. | |
| 2014/0066904 A1 | 3/2014 | Young | |
| 2014/0081243 A1 | 3/2014 | Zhou et al. | |
| 2014/0249508 A1 | 9/2014 | Wang et al. | |
| 2014/0276618 A1 * | 9/2014 | Di Caprio | A61M 25/0102 604/528 |
| 2014/0283355 A1 | 9/2014 | Chin et al. | |
| 2016/0121080 A1 | 5/2016 | Cottone | |
| 2016/0121086 A1 | 5/2016 | Castro et al. | |
| 2016/0296356 A1 | 10/2016 | Jordan et al. | |
| 2016/0346508 A1 | 12/2016 | Williams et al. | |
| 2017/0189041 A1 | 7/2017 | Cox et al. | |
| 2017/0319232 A1 | 11/2017 | Kiev | |
| 2017/0354800 A1 | 12/2017 | O'Donovan | |
| 2019/0255299 A1 | 8/2019 | Fischell et al. | |
| 2019/0306603 A1 | 10/2019 | Litovsky et al. | |
| 2019/0336149 A1 * | 11/2019 | Yang | A61M 25/0662 |
| 2019/0366056 A1 | 12/2019 | Mcevoy | |
| 2023/0256210 A1 | 8/2023 | Mcevoy et al. | |

FOREIGN PATENT DOCUMENTS

| | | |
|---|---|---|
| CN | 103252014 B | 12/2016 |
| CN | 206491909 U | 9/2017 |
| EP | 0303487 A2 | 2/1989 |
| EP | 0808637 A2 | 11/1997 |
| GB | 2494905 A | 3/2013 |
| JP | 2005514115 A | 5/2005 |
| JP | 2007503929 A | 3/2007 |
| JP | 2008536640 A | 9/2008 |
| JP | 2015147080 | 8/2015 |
| JP | 2015523186 A | 8/2015 |
| JP | 2016517320 A | 6/2016 |
| WO | 2003004085 A2 | 1/2003 |
| WO | 2003057273 A2 | 7/2003 |
| WO | 2005035226 A2 | 4/2005 |
| WO | 2006113868 A2 | 10/2006 |
| WO | 20100123371 A1 | 10/2010 |
| WO | 2011086758 A1 | 7/2011 |
| WO | 2014022310 A1 | 2/2014 |
| WO | 2014043694 A1 | 3/2014 |
| WO | 2014152191 A1 | 9/2014 |
| WO | 2017059186 A1 | 4/2017 |

OTHER PUBLICATIONS

Medtronic Launches Telescope(TM) Guide Extension Catheter to Support Complex Coronary Cases, https://finance.yahoo.com/news/medtronic-launches-telescope-tm-guide-133201972.html, May 16, 2019, 4 pp.

Office Action from counterpart Chinese Application No. 201980037946.6 dated Mar. 31, 2023, 14 pp.

Office Action, and translation thereof, from counterpart Japanese Application No. 2020-563709 dated Feb. 24, 2023, 10 pp.

PCT/US2019/035634, The International Search Report and Written Opinion, mailed Sep. 24, 2019, 55pgs.

PCT/US2019/035637, The International Search Report and Written Opinion, mailed Sep. 30, 2019, 13pgs.

PCT/US2019/035645, The International Search Report and Written Opinion, mailed Sep. 24, 2019, 20pgs.

PCT/US2019/035648, The International Search Report and the Written Opinion, mailed Sep. 24, 2019, 15pgs.

Prosecution History from U.S. Appl. No. 16/432,763, now issued U.S. Pat. No. 11,911,573, dated Mar. 2, 2021 through Nov. 16, 2023, 221 pp.

Second Office Action and Search Report from counterpart Chinese Application No. 201980037946.6 dated Nov. 4, 2022 15 pp.

* cited by examiner

MEDICAL CATHETER

This application is a continuation of U.S. patent application Ser. No. 16/432,763, filed on Jun. 5, 2019, and entitled, "MEDICAL CATHETER," which claims the benefit of U.S. Provisional Application No. 62/680,792, filed Jun. 5, 2018, and entitled, "MEDICAL CATHETER," and U.S. Provisional Patent Application No. 62/848,926, filed May 16, 2019, and entitled, "MEDICAL CATHETER." The entire contents of each of U.S. patent application Ser. No. 16/432,763, U.S. Provisional Application No. 62/680,792, and U.S. Provisional Patent Application No. 62/848,926 are incorporated herein by reference.

TECHNICAL FIELD

This disclosure relates to a medical catheter.

BACKGROUND

A medical catheter defining at least one lumen has been proposed for use with various medical procedures. For example, in some cases, a medical catheter may be used to deliver a medical device and/or composition within vasculature of a patient.

SUMMARY

In some aspects, this disclosure describes example catheters that each include a push assembly and an elongate body including an inner liner defining an entry port into a lumen of the elongate body and an outer jacket. The push assembly may include an elongate member and an anchor member positioned at a distal end of the elongate member. The elongate member is relatively stiff such that the push assembly may be configured to facilitate introduction of the catheter in vasculature of a patient. When the push assembly is assembled with the elongate body, distal to the entry port, a portion of the push assembly including the anchor member may be positioned between adjacent portions of the inner liner and outer jacket. Proximal to the entry port, a portion of the push assembly may be positioned outside of adjacent portions of the inner liner and outer jacket. In some examples, a proximal portion of the push assembly may be positioned entirely outside of the inner liner and outer jacket. In some examples, the anchor member may have a partial-ring shape and a beveled distal edge and may extend partially around an outer perimeter of the inner liner.

In some examples, a catheter system includes an outer catheter, and the catheter including the push assembly may be an inner catheter that may be introduced into vasculature of a patient through a lumen of the outer catheter. The elongate body may be configured to extend out of a distal opening of the outer catheter to extend through heavy tortuosity or calcification within a body vessel. The elongate body may have a smaller radial profile and may be more flexible than the outer catheter such that it may more easily navigate through heavy tortuosity or calcification within a body vessel than the outer catheter. In some examples, the elongate body may include an atraumatic tip to minimize adverse interactions with patient tissue during advancement of the elongate body within a body vessel.

In some aspects, this disclosure describes example catheters that each include a distal tip portion configured to reduce impact force between the distal tip of the catheter and tissue of a patient as the catheter is advance through vasculature of a patient. The distal tip portion may include a construction that reduces an effective durometer of the tip compared to a more proximal portion of the catheter. For example, the distal tip portion may include a tip outer jacket that includes a material or mixture of materials that has a lower durometer than an outer jacket of a more proximal portion of the catheter. As another example, an inner liner may end proximal of the distal tip, reducing an effective durometer of the distal tip portion.

Clause 1: A catheter comprising: an elongate body comprising: a proximal portion including a proximal end; and a distal tip portion, wherein the distal tip portion comprises: an inner liner; a marker band circumferentially surrounding the inner liner and extending from a marker band proximal end to a marker band distal end; an outer jacket circumferentially surrounding a first portion of the inner liner and ending proximal of the marker band proximal end; and a tip outer jacket circumferentially surrounding a second portion of the inner liner and the marker band, wherein the tip outer jacket extends distally past the marker band distal end to a distal tip of the elongate body, and wherein a proximal end of the tip outer jacket is laterally adjacent to a distal end of the outer jacket.

Clause 2: The catheter of clause 1, further comprising an elongate push member mechanically coupled to a proximal end of the elongate body.

Clause 3: The catheter of clause 1 or 2, wherein the elongate body defines at least one lumen extending from adjacent to or at the proximal end to adjacent to or at the distal tip.

Clause 4: The catheter of any one of clauses 1 to 3, wherein the inner liner extends to the distal tip of the elongate body.

Clause 5: The catheter of any one of clauses 1 to 3, wherein the inner liner ends distal to the marker band distal end and proximal to the distal tip.

Clause 6: The catheter of any one of clauses 1 to 3, wherein the inner liner ends at about the marker band distal end and proximal to the distal tip.

Clause 7: The catheter of any one of clauses 1 to 6, wherein the tip outer jacket extends between about 1.5 mm and about 3.0 mm distal of the marker band distal end.

Clause 8: The catheter of any one of clauses 1 to 7, wherein the tip outer jacket extends between about 1.5 mm and about 3.0 mm proximal of the marker band proximal end.

Clause 9: The catheter of any one of clauses 1 to 8, wherein the marker band defines a length of between about 0.5 mm and about 1.2 mm between the marker band proximal end and the marker band distal end.

Clause 10: The catheter of any one of clauses 1 to 9, wherein the proximal end of the tip outer jacket laterally abuts the distal end of the outer jacket.

Clause 11: The catheter of any one of clauses 1 to 10, wherein the proximal end of the tip outer jacket is bonded to the distal end of the outer jacket.

Clause 12: The catheter of any one of clauses 1 to 11, wherein the tip outer jacket exhibits a lower durometer than the outer jacket.

Clause 13: The catheter of any one of clauses 1 to 12, further comprising a reinforcement member circumferentially surrounding the inner liner, wherein the reinforcement member does not extend distally past the marker band distal end.

Clause 14: The catheter of clause 13, wherein a distal end of the reinforcement member overlaps the marker band.

Clause 15: The catheter of clause 13, wherein a distal end of the reinforcement member is proximal of the marker band proximal end.

Clause 16: The catheter of clause 13, wherein a distal end of the reinforcement member is substantially aligned with the marker band proximal end.

Clause 17: The catheter of any one of clauses 13 to 16, wherein the reinforcement member comprises a coil.

Clause 18: The catheter of clause 17, wherein the proximal portion comprises the coil, wherein coil defines a first pitch in the proximal portion, wherein the coil defines a second pitch in the distal tip portion, and wherein the second pitch is greater than the first pitch.

Clause 19: The catheter of any one of clauses 1 to 18, further comprises a hydrophilic coating on the outer jacket and the tip outer jacket.

Clause 20: The catheter of any one of clauses 1 to 19, wherein the outer jacket comprises a first poly(ether-block-amide), and wherein the tip outer jacket comprises a second, different poly(ether-block-amide).

Clause 21: The catheter of any one of clauses 1 to 19, wherein the outer jacket comprises a mixture of a first poly(ether-block-amide) and a second poly(ether-block-amide), and wherein the tip outer jacket comprises a third, different poly(ether-block-amide).

Clause 22: A catheter comprising: an elongate body comprising: a proximal portion including a proximal end; and a distal tip portion, wherein the distal tip portion comprises: an inner liner; a marker band circumferentially surrounding the inner liner and extending from a marker band proximal end to a marker band distal end; a reinforcement member circumferentially surrounding the inner liner, wherein the reinforcement member does not extend distally past the marker band distal end; and an outer jacket circumferentially surrounding a first portion of the reinforcement member and ending proximal of the marker band proximal end, wherein the inner liner ends at or distal to the marker band distal end and proximal to the distal tip, and wherein the outer jacket is the only layer distal of the distal end of the inner liner.

Clause 23: The catheter of clause 22, further comprising an elongate push member mechanically coupled to a proximal end of the elongate body.

Clause 24: The catheter of clause 22 or 23, wherein the elongate body defines at least one lumen extending from proximal the proximal end to proximate the distal tip.

Clause 25: The catheter of any one of clauses 22 to 24, wherein the inner liner ends at about the marker band distal end and proximal to the distal tip.

Clause 26: The catheter of any one of clauses 22 to 25, wherein the outer jacket extends between about 1.5 mm and about 3.0 mm distal of the marker band distal end.

Clause 27: The catheter of any one of clauses 22 to 26, wherein the marker band defines a length of between about 0.5 and about 1.2 mm between the marker band proximal end and the marker band distal end.

Clause 28: The catheter of any one of clauses 22 to 27, wherein a distal end of the reinforcement member overlaps the marker band.

Clause 29: The catheter of any one of clauses 22 to 27, wherein a distal end of the reinforcement member is proximal of the marker band proximal end.

Clause 30: The catheter of any one of clauses 22 to 27, wherein a distal end of the reinforcement member is substantially aligned with the marker band proximal end.

Clause 31: The catheter of any one of clauses 22 to 30, wherein the reinforcement member comprises a coil.

Clause 32: The catheter of clause 31, wherein the proximal portion comprises the coil, wherein coil defines a first pitch in the proximal portion, wherein the coil defines a second pitch in the distal tip portion, and wherein the second pitch is greater than the first pitch.

Clause 33: The catheter of any one of clauses 22 to 32, further comprises a hydrophilic coating on the outer jacket and the tip outer jacket.

Clause 34: A method of using the catheter of any of clauses 1-33.

Clause 35: A method of manufacturing the catheter of any of clauses 1-33.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
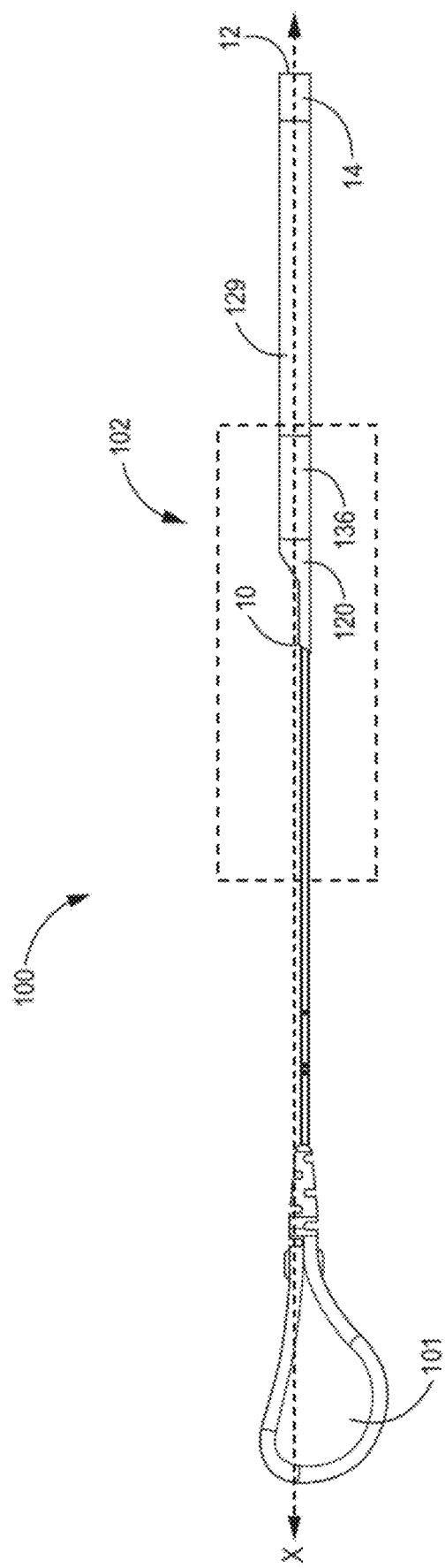
FIG. 1 is a conceptual side view of an example catheter, which includes an elongate body, a push assembly, and a handle.

In some examples, a medical catheter ("catheter") described herein includes a push assembly and an elongate body including an inner liner and an outer jacket. The push assembly includes an elongate member (also referred to herein as a shaft) and an anchor member at a distal end of the push assembly. In some examples, the push assembly includes only one anchor member at the distal end of the push assembly, while in other examples, the push assembly includes a plurality of anchor members. The anchor member is configured to facilitate attachment of the elongate member to the inner liner and outer jacket of the elongate body. The anchor member may be positioned at a distal end of the elongate member.

The outer jacket and the inner liner, alone or in combination with other elements, may form the elongate body, may be a distal portion of the catheter. The elongate body defines at least one lumen through which a medical device (e.g., a catheter, guidewire, filter, stent delivery system, and the like), therapeutic agent, or other element can be introduced into vasculature or other tissue sites of a patient. The inner liner may define an entry port into the lumen. At least a portion of the elongate member of the push assembly may extend proximal of the outer jacket and the inner liner. In examples in which the catheter is part of an intravascular catheter system and is used in conjunction with an outer catheter, the elongate body of the catheter may be used to effectively extend the reach of the outer catheter. For example, the elongate body of the catheter may be fully or partially pushed through a lumen of the outer catheter until the entire or part of the elongate body extends past a distal end of the outer catheter, while the push assembly remains fully or partially within the lumen of the outer catheter. The push assembly has a lower profile than the elongate body, and, as a result, may occupy less space within the outer catheter lumen than the elongate body of the catheter. Thus, the push assembly may both facilitate pushability of the catheter through the outer catheter and/or through vasculature of a patient, while still enabling relatively large medical devices to be introduced through the outer catheter lumen to reach the lumen of the catheter.

In some examples, the catheter described herein may also help delivery to or past a diseased region or the body. For example, a diseased region may include heavy tortuosity and/or calcification and the catheter may be better suited for navigation through such heavy tortuosity and/or calcification than the outer catheter due to its flexibility and lower profile. In some examples, a clinician may push the catheter out of a distal end of the outer catheter upon the approach of the outer catheter to such a region that would be difficult or impossible for the outer catheter to extend through. In some examples, the catheter may be said to "telescope" out of the outer catheter when it is pushed out of a distal end of the outer catheter.

The elongate body, including the inner liner and outer jacket, may define a proximal end. Distal to the proximal end, a portion of the push assembly including the anchor member may be positioned between the inner liner and outer jacket. The anchor member may extend only partially around an outer perimeter of the inner liner. Proximal to the proximal end of the elongate body, a portion of the push assembly proximal to the portion including the anchor member may be positioned outside of the outer jacket.

In some examples, the anchor member may be configured to facilitate manufacture of a catheter. For example, the anchor may define a beveled distal edge to assist with placement of the anchor member, including insertion and advancement of the anchor member between the outer jacket and the inner liner. As another example, the anchor member may define a slot extending from a proximal end of the anchor member and towards a distal end of the anchor member. The slot may facilitate attachment of the elongate member to the anchor member as the slot may be configured such that a distal end of the elongate member may be positioned at least partially within the slot and may be welded to the anchor. The slot may be configured such that welding material may be placed between the anchor member and the elongate member, such as in a gap within the slot between the anchor member and the elongate member when the distal end of the elongate member is positioned at least partially within the slot, such that the welding material may not add to the profile of the push assembly.

In some examples, an inner surface and/or an outer surface of the anchor member may be a non-semicircular surface such as, for example, a surface defining a plurality of notches or waves and/or a textured and/or etched surface. Such a non-circular surface may aid in securing the anchor member between the inner liner and the outer jacket by providing greater surface area that may be bonded to the inner liner and/or outer jacket including, for example, by reflow of material of the inner liner and/or outer jacket.

In some examples, the catheter may include one or more radiopaque markers to facilitate visualization of the catheter during a medical procedure. The one or more radiopaque markers can be located, for example, on the anchor member, on the elongate member, or in any suitable place or combination of places, to assist with visualization and placement of the catheter, with respect to, for example, an outer catheter and/or a target tissue site. In some examples, the anchor is at least partially radiopaque and/or a radiopaque marker is positioned at or near the entry port into the elongate body of the catheter. This radiopaque marker placement may enable a clinician to relatively quickly ascertain the location of the entry port of the lumen of the catheter.

In some examples, the catheter may be configured to facilitate maneuverability. For example, the outer jacket may vary in stiffness along its length, which may help aid maneuverability of the catheter within vasculature of a patient. As another example, a reinforcement member may be positioned between the inner liner and the outer jacket, may be distal to and/or abutting the anchor member, and may aid in the strength and/or maneuverability of the catheter within vasculature of a patient.

In some examples, the elongate member of the push assembly may taper in a distal direction to enable the distal portion of the elongate member to better approximate a profile of the anchor member. By tapering the elongate member instead of forming the entire elongate member to have the lower profile, the proximal portion of the elongate member may still have a size and strength sufficient for pushing the catheter within the vasculature and/or sufficient size for gripping by a user. In some of these examples, as well as some other examples, the elongate member may be a solid member having a round (e.g., circular) cross-section. That is, the elongate member may not define a central lumen or other opening in its cross-section.

In some examples, the catheter may facilitate differentiation from other devices used in conjunction with the catheter and/or between elements of the catheter. For example, a sleeve may surround at least a portion of the elongate member, such as a portion proximal to the anchor member. In some examples, the sleeve may be a different color than the elongate member, the elongate body, a guidewire, and/or other devices used with the catheter in order to help visually distinguish the sleeve. The sleeve can also include other features to help facilitate usage of the sleeve. For example, the sleeve may include one or more bands including one or more partial cuts extending partially through a radial thickness of the sleeve and/or one or more markers. In some examples, the sleeve may include a textured surface. In some examples, partial cuts and/or a textured surface may aid in tactile differentiation of the sleeve from other components. In some examples, one or more bands including one or more partial cuts and/or markers may aid in visual differentiation of the sleeve. Visual and/or tactile differentiation of the sleeve may enable the elongate member to be discerned from other elements including, for example, an outer catheter, a guidewire, or other delivery devices or components in use with the catheter described herein.

Figure 2:
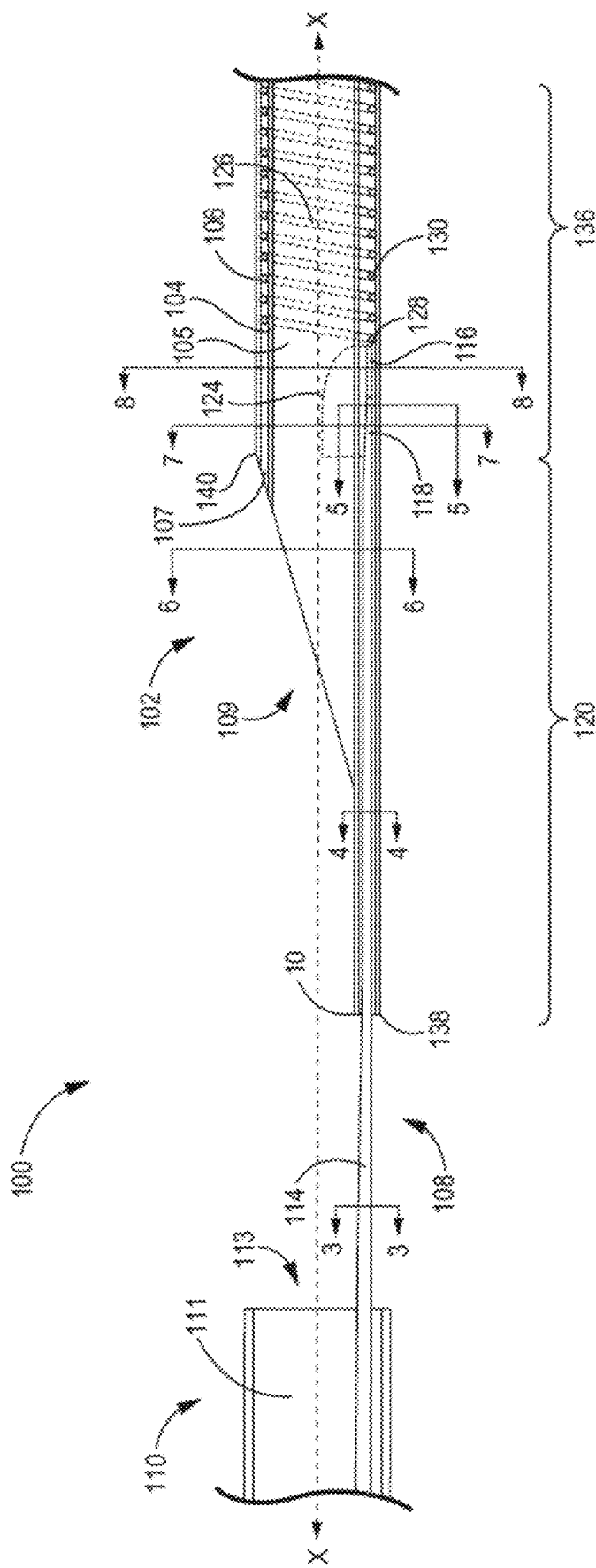
FIG. 2 is a conceptual cross-sectional view of a portion of the example catheter of FIG. 1 and an outer catheter.

FIG. 1 is a conceptual side view of an example catheter 100, which includes an elongate body 102, a push assembly 108, and a handle 101. FIG. 2 is a conceptual cross-sectional view of a portion of catheter 100 of FIG. 1 and an outer catheter 110. Catheter 100 defines a longitudinal axis X. Elongate body 102 includes an inner liner 104 and an outer jacket 106. As shown in FIG. 1, elongate body 102 may define a proximal end 10 and a distal end 12.

In some examples, catheter 100 may be part of an assembly that includes an outer catheter 110 defining a lumen 111, through which catheter 100 may be introduced in order to access, for example, a distal target site within vasculature of a patient. Thus, at least a portion of outer catheter 110 may be configured to surround catheter 100. Outer catheter 110 may further define distal opening 113 and, in some examples, at least a portion of catheter 100 may be configured to extend through distal opening 113 and distally of outer catheter 110, as shown in FIG. 2. For example, catheter 100 may be configured to extend out of distal opening 113 of outer catheter 110 to extend through heavy tortuosity or calcification within a body vessel. Catheter 100 may have a smaller radial profile and may be more flexible than outer catheter 110 such that it may more easily navigate through heavy tortuosity or calcification within a body vessel than outer catheter 110.

In some examples, an outer radial profile of elongate body 102 of catheter 100 may be similar in a radial shape and/or size of at least a distal portion of lumen 111 of outer catheter 110 such that catheter 100 may fit relatively snugly inside of outer catheter 110 when elongate body is at least partially within outer catheter 110. This may help to define a relatively smooth transition between elongate body 102 and outer catheter 110 when only a portion of elongate body 102 extends distally of distal opening 113 of outer catheter 110 and another portion remains within lumen 111 of outer catheter 110 and/or when a proximal end of elongate body 102 abuts a distal end of outer catheter 110. This relatively smooth transition and/or snug fit may provide certain advantages. For example, fluids may be easier to deliver through the lumen 111 of outer catheter 110 and the lumen 105 of elongate body 102 without leakage. As an additional example, devices and/or other elements may be easier to advance from lumen 111 of outer catheter 110 to lumen 105 of elongate body 102 because the transition between lumen 111 and lumen 105 may be relatively smooth such that components being delivered may not get caught at a transition from lumen 111 to lumen 105.

Although catheter 100 is shown as extending out distal opening 113 of outer catheter 100 such that proximal end 10 of elongate body 102 is distal to distal opening 113, in some medical procedures, catheter 100 may be positioned relative to outer catheter 110 such that proximal end 10 of elongate body 102 is proximate to distal opening 113. For example, entry port 109 of elongate body 102, described in further detail below, may be positioned within lumen 111 of outer catheter 110, such that an interventional medical device or another medical device can be introduced from lumen 111 of outer catheter 110 into lumen 105 of elongate body 102 without exiting lumen 111.

In some examples, as shown in FIG. 1, catheter 100 may include an atraumatic tip 14 to minimize adverse interactions with patient tissue during advancement of catheter 100 within a body vessel.

Elongate body 102 is configured to provide a delivery vessel on catheter 100 that may extend distally of outer catheter 110 to telescope out of a distal end of outer catheter 110 and effectively extend a reach of a catheter within vasculature of a patient and enable delivery of devices, agents, and/or any other suitable elements to target sites that may be difficult for outer catheter 110 to reach. In some examples, elongate body 102 may include an inner liner 104 and outer jacket 106 that may provide multiple layers between which push assembly 108 may be inserted to attach push assembly 108 to elongate body 102. This may provide for a relatively strong attachment between push assembly 108 and elongate body 102, as well as maintain relatively smooth outer and inner surfaces of elongate body 102 at the portion of elongate body 102 attached to push assembly 108.

Inner liner 104 of elongate body 102 defines lumen 105 and outer jacket 106 defines lumen 107. In some examples, at least a portion of inner liner 104 may be positioned within lumen 107 of outer jacket 106. In some examples, inner liner 104 may extend within the full length of lumen 107 of outer jacket 106. In other examples, however, inner liner 104 may terminate prior to a distal end of outer jacket 106 or may extend past a distal end of outer jacket 106. Although elongate body 102 is shown as a tubular body in FIG. 1, elongate body 102 may have any suitable configuration.

Inner liner 104, alone or in combination with outer jacket 106, may define entry port 109 into lumen 105. Entry port 109 may extend from a proximal end 138 to a distal end 140 along a length of elongate body 102. In some examples, entry port 109 may be angled from distal end 140 to proximal end 138 due to the tapered shape of the elongate body 102. Entry port 109 may be formed by skiving at least part of portion 120 of elongate body 102. In some examples, entry port 109 may have a length, measured from proximal end 138 to distal end 140 along longitudinal axis X, of about 2 centimeters (cm) to about 10 cm (e.g., 2 cm to 10 cm or nearly 2 cm to 10 cm, to the extent permitted by manufacturing tolerances), such as about 3.5 cm to about 4.5 cm or about 4 cm. It is believed that a tapered entry port 109 having a relatively longer length and being angled from distal end 140 to proximal end 138 may help contribute to smooth delivery of a medical device (e.g., an interventional medical device) into inner lumen 105 of elongate body 102 via entry port 109 by guiding the medical device into inner lumen 105.

Push assembly 108 may be configured to enable a clinician to position elongate body 102 with respect to outer catheter 110 and/or with respect to patient vasculature. For example, a proximal portion of push assembly 108 may be configured to be gripped and moved by the clinician to position (e.g., advance distally or proximally, and/or rotate) elongate body 102 within vasculature of a patient. In some examples, push assembly 108 may be used to advance elongate body 102 with respect to outer catheter 110 to advance elongate body 102 within outer catheter 110 and/or extend all or a portion of elongate body 102 distal of outer catheter 110 to access vasculature distal to outer catheter 110. Push assembly 108 may include any suitable length. In some examples, a length of push assembly 108 may be approximately 100 cm to approximately 150 cm, such as about 125 cm, measured along longitudinal axis X and from a distal end of handle 101 to a distal end 128 of anchor or measured from a distal end of handle 101 to a distal end of elongated member 114. In some examples, push assembly 108 includes an elongate member 114 and an anchor member 116. For clarity, a portion of anchor member 116, which is positioned behind inner liner 104 in the illustrated view, is shown in phantom. In some examples, elongate member 114 may include a distal end 118 and anchor member 116 may be positioned at distal end 118 of elongate member 114. In some examples, push assembly 108 may not include any other anchor member at distal end 118 other than anchor member 116.

In some examples, at least a portion of push assembly 108 is positioned between at least adjacent portions (e.g., radially adjacent portions) of inner liner 104 and outer jacket 106. For example, at least a portion of push assembly 108 may be positioned radially inward of outer jacket 106 and radially outward of inner liner 104 such that the portion of push assembly 108 is between outer jacket 106 and inner liner 104. In some examples, the portion of push assembly 108 between inner liner 104 and outer jacket 106 may have a length of approximately 4 cm. Positioning at least a portion of push assembly 108 between portions of inner liner 104 and outer jacket 106 may aid in mechanically connecting push assembly 108 and elongate body 102 in a manner that enables push assembly 108 to transmit pushing forces and, in some examples, rotational forces, to elongate body 102. In addition, positioning at least a portion of push assembly 108 between inner liner 104 and outer jacket 106 may enable elongate body 102 to have relatively smooth inner and outer surfaces at the portion of elongate body 102 attached to push assembly 108.

In some examples, elongate body 102 may include a tapered portion 120. For example, portions of inner liner 104 and outer jacket 106, as shown in FIG. 2, corresponding to tapered portion 120 of elongate body 102 may be tapered in a proximal direction. The tapering of elongate body 102 at tapered portion 120 may enable elongate body 102 to more easily be retracted into outer catheter 110. For example, during or after use of catheter 100, a clinician may desire to retract at least a portion of elongate body 102 within outer catheter 110 by retracting push assembly 108 proximally with respect to outer catheter 110. Tapered portion 120 may allow for smoother entry of elongate body 102 into outer catheter 110.

Additionally, the tapered shape of tapered portion 120 may be configured facilitate attachment of push assembly 108 to elongate body 102. For example, the tapered shape may allow for anchor member 116 to support entry port 109 while also allowing a portion of elongate member 114 proximal to anchor member 116 to be positioned between inner liner 104 and outer jacket 106, which may increase bond tensile strength between the push assembly 108 and the elongate body 102. The bond tensile strength between push assembly 108 and elongate body 102 may decrease with a shorter length of elongate member 114 positioned between inner liner 104 and outer jacket 106. Thus, if only anchor member 116 (and not elongate member 114) was positioned between inner liner 104 and outer jacket 106, then the bond tensile strength between push assembly 108 and elongate body 102 may decrease. The decreased bond tensile strength may adversely affect the ability for push assembly 108 to transfer pushing and/or rotational forces to elongate body 102 without compromising the mechanical connection between push assembly 108 and elongate body 102.

Further, because a distal portion of elongate member 114 may be relatively flexible (compared to a more proximal portion of elongate member 114), as described in further detail below, positioning the distal portion of elongate member 114 between inner liner 104 and outer jacket 106 may help prevent the junction of push assembly 108 and elongate body 102 from being undesirably stiff.

In some examples, distal to proximal end 10 of elongate body 102, a portion of push assembly 108 is positioned between adjacent portions of inner liner 104 and outer jacket 106. Proximal to proximal end 10 of elongate body 102, a portion of push assembly 108 is positioned outside of outer jacket 106 and inner liner 104. The portion of push assembly 108 positioned between adjacent portions of inner liner 104 and outer jacket 106 may comprise anchor member 116. The portion of push assembly 108 positioned outside of outer jacket 106 and inner liner 104 may be proximal to the portion positioned between adjacent portions of inner liner 104 and outer jacket 106.

Anchor member 116 may have any suitable shape and size. In some examples, at least an outer surface of anchor member 116 may define a partial-ring shape as shown in further detail below with reference to FIGS. 6-9. In other examples, however, anchor member 116 may define other shapes. The partial-ring shape of anchor member 116 may provide one or more advantages. For example, the partial-ring shape may provide support to inner liner 104 and outer jacket 106 to prevent collapse of proximal ends of inner liner 104 and outer jacket 106 and thus help maintain the open state of entry port 109 into lumen 105 defined by inner liner 104 such that other catheters or devices may be inserted into lumen 105.

In some examples, and as described in further detail below with respect to FIG. 6, anchor member 116 may have an inner perimeter that is less than the outer perimeter of inner liner 104 and anchor member 116 may extend only partially around an outer perimeter of inner liner 104. For example, anchor member 116 may extend about 140 degrees to about 160 degrees around an outer perimeter of inner liner 104. More particularly, in some examples, anchor member 116 may extend about 160 degrees around the outer perimeter of inner liner 104. In some examples, anchor member 116 is radiopaque, and extending only partially about the outer perimeter of inner liner 104 may enable anchor member 116 to indicate a rotational orientation (e.g., rotational position about longitudinal axis X) of elongate body 102 (e.g., entry port 109) within vasculature of a patient. This may enable a clinician to better position catheter 100 relative to outer catheter 110.

In addition, extending only partially about the outer perimeter of inner liner 104 may enable anchor member 116 to be positioned within tapered portion 120 of elongate body 102. This may enable anchor member 116 to be positioned at entry port 109 to indicate the location thereof, and may also enable anchor member 116 to provide structural support to tapered portions of the inner liner 104 and outer jacket 106. A full-ring shape would not be able to be located within the tapered portion 120 of elongate body 102 but instead would need to be located distal to the tapered portion 120 and thus distal to the entry port 109 in order to fit between inner liner 104 and outer jacket 106 without being exposed and would thus not be able to include a marker to indicate a location of the entry port 109.

In some examples, however, as shown in FIG. 2, a proximal end of anchor member 116 is positioned proximate to the distal end 140 of entry port 109. For example, a proximal end of anchor member 116 may be aligned with distal end 140 of entry port 109, such that anchor member 116 is fully positioned within the portion of elongate body 102 defining a circular outer perimeter in cross-section. As another example, a proximal end of anchor member 116 may not be exactly aligned with distal end 140 of entry port 109, but within 4 millimeters (mm), such as within 2 mm or less, of distal end 140 of entry port 109 in a proximal or a distal direction. In these examples, a substantial length of that anchor member 116 is positioned within the portion of elongate body 102 defining a circular outer perimeter in cross-section.

This partial-ring shape of anchor member 116 may also be advantageous over a full-ring shape because it may be less likely to cause inner liner 104 to bunch during insertion of anchor member 116 between outer jacket 106 and inner liner 104 because anchor member 116 does not extend fully about an outer perimeter of inner liner 104.

In some examples anchor member 116 may define a beveled distal edge 124. Beveled distal edge 124 may allow anchor member 116 to more easily be inserted and advanced between inner liner 104 and outer jacket 106 than examples in which an anchor member has a straight edge. For example, beveled distal edge 124 may enable anchor member 116 to be more easily inserted between inner liner 104 and outer jacket 106 by providing a narrow profile of anchor member 116 at distal end 128, which leads anchor member 116 into the space between inner liner 104 and outer jacket 106. Additionally, beveled distal edge 124 may provide a smooth distal profile of anchor member 116 that enables less resistance to advancement of anchor member 116 between and with respect to inner liner 104 and outer jacket 106 than a profile including a straight edge and/or sharp corners which may be more likely to catch on inner liner 104 and/or outer jacket 106.

Inner liner 104 may be formed from any suitable material, such as, but not limited to polytetrafluorethylene (PTFE). In some examples, outer jacket 106 may comprise one or more polymers. In some examples, outer jacket 106 may have a hydrophilic coating. For example, the hydrophilic coating may be positioned over the entire outer surface of outer jacket 106 or only along a portion of outer jacket, such as only along a distal-most portion of outer jacket 106. In some examples, a hydrophilic coating is positioned over the distal-most approximately 15 cm to approximately 25 cm of outer jacket 106 (e.g., the distal-most 15 cm to 25 cm to the extent permitted by manufacturing tolerances), such as the distal-most approximately 20 cm to approximately 22 cm of outer jacket 106, or the distal-most approximately 21 cm of outer jacket 106, the distances being measured from distal end of outer jacket 106, which may correspond to distal end 12 of elongate body 102 in some examples.

In some examples, outer jacket 106 may include multiple sections having different stiffnesses. For example, outer jacket 106 may include a proximal section, corresponding with portion 136 of catheter 100, and a distal section, corresponding with portion 129 of catheter 100 (shown in FIG. 1), that is distal to the proximal section. In some examples, the proximal section may be approximately 1 cm to approximately 4 cm long, such as approximately 2.5 cm long or approximately 1.25 cm long. In some examples, the distal section may be approximately 15 cm to approximately 27 cm long, such as approximately 24 cm long to approximately 26 cm long, or approximately 25 cm long. The lengths may be measured along longitudinal axis X.

The distal section of outer jacket 106 may have a different stiffness than the proximal section. For example, the distal section may have a stiffness that is greater than a stiffness of the proximal section. In other examples, the distal section may have a stiffness that is less than the proximal section. Outer jacket 106 having a more stiff proximal section (relative to a distal outer jacket section) may help maintain the integrity of the proximal portion of inner lumen 105 of elongate body 102, which may aid in introduction of medical devices into lumen 105 from entry port 109 without adversely impact the navigability of catheter 100 through vasculature of a patient. For example, outer jacket 106 having a more stiff proximal section may help distal end 140 of entry port 109 and a proximal-most portion of elongate body 102 resist deformation to help maintain lumenal integrity.

Outer jacket 106 may include any suitable number of sections having any suitable stiffnesses according to particular needs. In some examples, sections of outer jacket 106 may include different types of polymers, with a stiffer section comprising a stiffer polymer than a more flexible section comprising a softer polymer. In some examples, outer jacket 106 having multiple sections with different stiffnesses may provide improved functionality of outer jacket 106 including, for example, improved maneuverability of outer jacket 106 through the vasculature. For example, the distal section may have a stiffness that is less than a stiffness of the proximal section, which may allow the distal section improved flexibility for navigation through the vasculature.

In some examples, catheter 100 may further include a reinforcement member 126 positioned between a portion of inner liner 104 and a portion of outer jacket 106. For clarity, a portion of reinforcement member 126, which is positioned behind inner liner 104 in the illustrated view, is shown in phantom. Reinforcement member 126 may be any suitable structure configured to provide structural support to elongate body 102 and, in some examples, increase the structural integrity of elongate body 102. For example, reinforcement member 126 may comprise a metal coil, a metal braid, or a combination thereof. In some examples, a distal end 128 of anchor member 116 may be positioned proximal to and spaced from reinforcement member 126, such that there is a gap between distal end 128 of anchor member 116 and a proximal end 130 of reinforcement member 126. Example gaps include, for example, gaps less than or equal to 4 mm, such as about 2 mm or less than 2 mm, measured along longitudinal axis X. In other examples, anchor member 116 may contact (e.g., abut) reinforcement member 126, e.g., distal end 128 of anchor member 116 may contact proximal end 130 of reinforcement member 126. In yet other examples, anchor member 116 and reinforcement member 126 may overlap in the longitudinal direction, e.g., by a length of about 2 mm or less, such as about 1 mm or less.

Anchor member 116 at distal end 118 of elongate member 114 may increase a surface area of a distal portion of push assembly 108 relative to examples of push assemblies including only elongate member 114 without anchor member 116, which may provide certain advantages. For example, the increased surface area at the distal portion of push assembly 108 provided by anchor member 116 may improve tensile strength of catheter 100 by strengthening the bond between push assembly 108 and elongate body 102. Additionally, the increased surface area at the distal portion of push assembly 108 provided by anchor member 116 may help prevent protrusion of elongate member 114 through outer jacket 106 when elongate member 114 is under compression, i.e., when a pushing force is applied to a proximal portion of elongate member 114 as catheter 100 is advanced through vasculature of a patient. For example, in examples without anchor member 116, distal end 118 of elongate member 114 may pierce outer jacket 106 due to the relatively small surface area of distal end 118 of elongate member 114. Anchor member 116, however, helps distribute the pushing force and minimize any pressure points at the distal end of push assembly 108. Additionally, anchor member 116 may help avoid bending of distal end 118 of elongate member 114 under outer jacket 106 by providing reinforcement to distal end 118 of elongate member 114.

Figure 3:
FIG. 3 is a conceptual cross-sectional view of an example elongate member of the push assembly of the catheter of FIGS. 1 and 2 taken along line 3-3 in FIG. 2.
Figure 4:
FIG. 4 is a conceptual cross-sectional view of an example elongate member of the push assembly of the catheter of FIGS. 1 and 2 taken along line 4-4 in FIG. 2.
Figure 5:
FIG. 5 is a conceptual cross-sectional view of an example elongate member of the push assembly of the catheter of FIGS. 1 and 2 taken along line 5-5 in FIG. 2.

FIGS. 3, 4, and 5 are conceptual cross-sectional views of an example elongate member 114 of push assembly 108 of catheter 100 of FIGS. 1 and 2 taken along lines 3-3, 4-4, and 5-5, respectively, in FIG. 2. Although lines 3-3, 4-4, and 5-5 are shown as intersecting multiple elements of catheter 100 in FIG. 1, for clarity, FIGS. 3, 4, and 5 show only the cross-section of elongate member 114. As shown, elongate member 114 may taper in a distal direction. For example, in some examples and as shown in the illustrated example, a greatest cross-sectional dimension of elongate member 114 along line 5-5 may be smaller than a greatest cross-sectional dimension of elongate member 114 along line 3-3 and a greatest cross-sectional dimension of elongate member 114 along line 4-4. In some examples and as shown in the illustrated example, a greatest cross-sectional dimension of elongate member 114 along line 4-4 may be smaller than a greatest cross-sectional dimension of elongate member 114 along line 3-3. A transition between the cross-sections illustrated in FIGS. 3, 4, and 5 may be stepwise, defined by a discrete tapered section, or defined by a substantially constant tapered section.

In some examples, a cross-section of a proximal portion of elongate member 114, such as the cross-section along line 3-3, may be round (e.g., circular). In some examples, this proximal portion of elongate member 114 having the round cross-section may include a proximal-most portion of elongate member 114 including a proximal end of elongate member 114. In addition, in some examples, the proximal portion of elongate member 114, the configuration of which may be represented by the cross-section along line 3-3, may be both round in cross-section and solid (e.g., not hollow or defining any lumens). Elongate member 114 having a proximal portion that is solid and round in cross-section may exhibit a better push force transmission along catheter 110, e.g., relative to an elongate body that has a proximal portion that is a hollow in cross-section and/or non-round (e.g., rectangular) in cross-section.

In some examples, a greatest cross-sectional dimension of the proximal portion of elongate member 114, e.g., as shown at line 3-3, is approximately 0.3 mm to approximately 1 mm, such as approximately 0.4 mm to approximately 0.5 mm. However, other cross-sectional dimensions of elongate member 114 may be used in other examples.

In some examples, as in the illustrated example, a portion of elongate member 114 having a circular cross section may be proximal to a portion of elongate member 114 having a D-shaped cross-section. The portions of elongate member 114 having the D-shaped cross-sections may define a smaller profile than the proximal portion of elongate member 114 defining the round (e.g., circular) cross-section, such that the portions of elongate member 114 defining the D-shaped cross-sections may define the "tapered" portions of elongate member 114. For example, a cross-section of an intermediate and/or a distal portion of elongate member 114, such as the cross-section along line 4-4 or line 5-5, may be D-shaped. In these examples, one half of elongate member 114 in cross-section may be substantially flat (e.g., planar to extent permitted by manufacturing tolerances) and the other longitudinal half of elongate member 114 in cross-section may be round (e.g., semi-circular).

In examples in which a distal portion of elongate member 114 tapers in a distal direction, a first section of the distal portion may define a first D-shaped cross section having a first cross-sectional area, e.g., a shown in FIG. 4, and a second section of the distal portion distal to the first section may define a second D-shaped cross section having a second cross-sectional area, where the second cross-sectional area is less than the first cross-sectional area.

The difference in cross-sectional area may be due to, for example, a profile height of elongate member 114 in the first and second sections of the distal portion. In some examples, a D-shaped cross-section along line 4-4 may include profile height (e.g., from the flat surface of the "D" to the crest of the curved surface of the "D") of approximately 0.1 mm to about 0.5 mm, such as approximately 0.2 mm to approximately 0.3 mm. In some examples, a D-shaped cross-section along line 5-5 is less than the profile height along line 4-4, and may include profile height of approximately 0.05 mm and 0.2 mm. Other profile heights may be used in other examples and may depend on various factors, such as a size of lumen 105 or anchor member 116. The profile height at the distal-most section of the distal portion of elongate member 114 may be selected such that when elongate member 114 is mechanically connected to anchor member 116, elongate member 114 does not protrude from anchor member 116 in the cross-sectional dimension (orthogonal to longitudinal axis X) or protrudes a relatively minimal amount from anchor member 116 to reduce occupying space that limits the cross-sectional size of lumen 105.

In some examples, a length of a proximal portion elongate member 114 having a circular cross section as illustrated in FIG. 3 may be approximately 100 cm to approximately 130 cm, such as approximately 110 cm to approximately 120 cm, or approximately 115 cm or approximately 117.5 cm. In some examples, the tapered portion of elongate member 114 adjacent to the proximal portion and extending to a distal end of elongate member 114 may have a length between approximately 2 cm to approximately 20 cm, such as approximately 10 cm.

In some examples, a length of elongate member 114 having a cross section substantially as illustrated along line 4-4 may be between approximately 20 mm to approximately 60 mm, such as approximately 40 mm. The cross-section along line 4-4 may be selected to enable elongate member 114 to be positioned between at least adjacent portions of inner liner 104 and outer jacket 106 and provide structural support to entry port 109.

In addition, in some examples (which may be combined with the foregoing dimensions), a length of elongate member 114 having a cross-section substantially as illustrated along line 5-5 may be between approximately 5 mm to approximately 15 mm, such as approximately 10 mm. The cross-section along line 5-5 may be selected to enable elongate member 114 to be positioned between at least adjacent portions of inner liner 104 and outer jacket 106 without obstructing inner lumen 105 of elongate body 102. In some examples, the distal-most section of elongate member 114 including a distal end of elongate member 114, e.g., represented by the cross-section shown in FIG. 5, may be selected to enable the distal portion of elongate member 114 to be flexible enough to be moved out of the way of a medical device that is being introduced into lumen 105 of elongated body 102 via entry port 109. As the medical device is pushed into lumen 105, elongate member 114 may inadvertently wrap around the medical device due to the manner in which it extends through outer catheter 110. This can be referred to as "wire wrap." The relatively flexible distal portion of elongate member 114 may enable the medical device to push past any wrapped sections of elongate member 114 and avoid adverse impacts to medical device delivery attributable to wire wrap.

In some examples, the cross-section along line 5-5 may be selected to substantially match a thickness of anchor member 116. This provide a smoother profile at the juncture of elongate member 114 and anchor member 116, which may result in a smoother profile of entry port 109 and lumen 105.

In some examples, a cross-section of elongate member 114 may be flat or substantially flat on one side (such as D-shaped) or on both sides at a portion that is distal to a portion having a circular cross section. A cross-section of elongate member 114 may have any suitable size and/or shape according to particular needs. In addition, elongate member 114 may be tapered using nay suitable technique. In some examples, the tapered cross-section of elongate member 114 may be defined by an abrasive processing, such as grinding, sanding, or grit blasting. In some examples, the abrasive processing to form the taper of elongate member 114 may form at least one rough surface on elongate member. The at least one rough surface may increase the surface area of elongate member 114. The increased surface area may improve adhesion of a polymeric material, such as PTFE, and decrease delamination of the polymeric material, for example, during use of catheter 100. The polymeric material may be, for example, the material used to form inner liner 104 and/or outer jacket 106.

Elongate member 114 being tapered in a distal direction may provide particular advantages in some cases. For example, a proximal portion of elongate member 114 having a solid round profile may have greater cross sectional area and mechanical integrity compared to an elongate member having a different profile, such as a rectangular profile or a hollow profile. In this way, the proximal portion of elongate member 114 may better resist kinking in response to a push force better than an elongate member having a different profile, such as a rectangular cross-section and/or a hollow cross-section. For example, a solid 0.45 mm diameter round profile stainless steel elongate member 114 may transfer at least 400 gram-force.

Additionally, or alternatively, due to its D-shaped tapered portions (e.g., alone lines 4-4 and 5-5), elongate member 114 may have greater flexibility at a distal portion (relative to non-D-shaped profiles, such as circular profiles), which may help facilitate navigability of catheter 100 through vasculature of a patient. The D-shaped profile may also enable elongate member 114 to have a similar profile to anchor member 116 at a portion of elongate member 114 bonded to anchor member 116 which may allow push assembly 108 to maintain a smoother profile at the juncture of elongate member 114 and anchor member 116. This smoother profile at the juncture of elongate member 114 and anchor member 116 may result in a smoother profile of entry port 109 and lumen 105, which may facilitate easier introduction of medical devices into lumen 105 via entry port 109.

Figure 6:
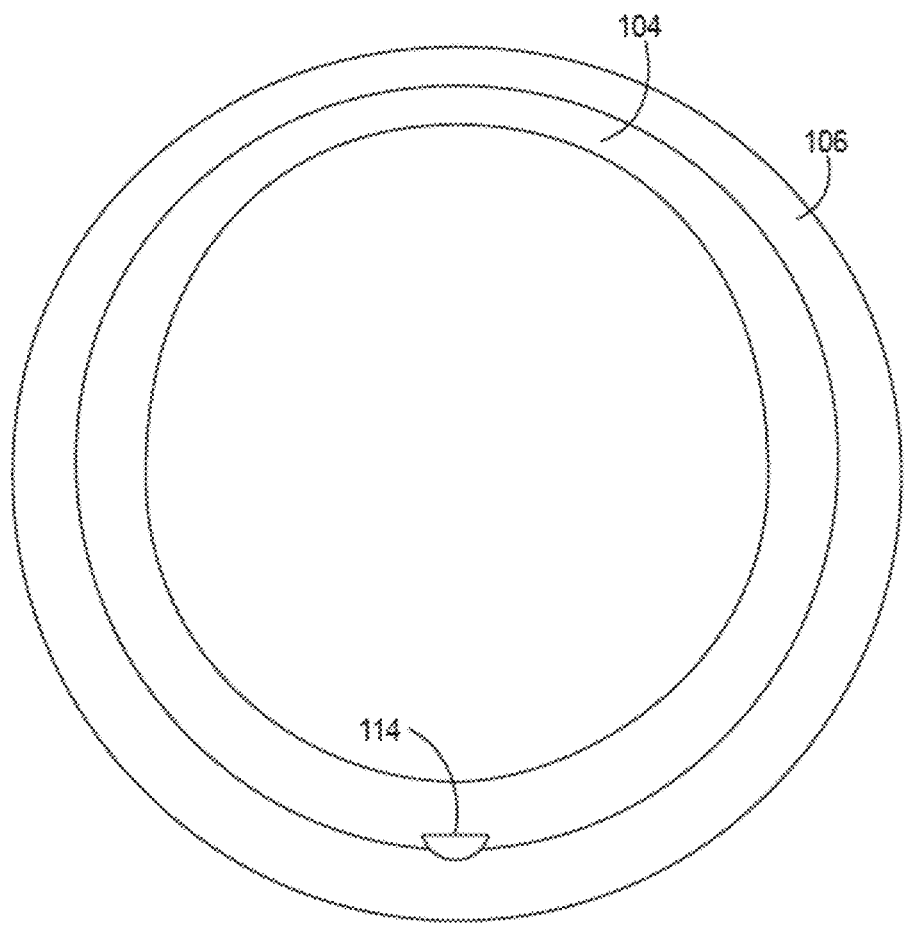
FIG. 6 is a conceptual cross-sectional view of the catheter of FIGS. 1 and 2 taken along line 6-6 in FIG. 2.

FIG. 6 is a conceptual cross-sectional view of catheter 100 of FIGS. 1 and 2 taken along line 6-6 in FIG. 2. FIG. 6 illustrates a cross-section of inner liner 104, outer jacket 106, and elongate member 114 within the section of catheter 100 defining entry port 109. Inner liner 104 and outer jacket 106 do not define circular cross-sections in the portion of catheter 100 shown in FIG. 6 because they are configured (e.g., by skiving) to define entry port 109. In addition, anchor body 116 is not present in the portion of catheter 100 shown in FIG. 6.

Figure 7A:
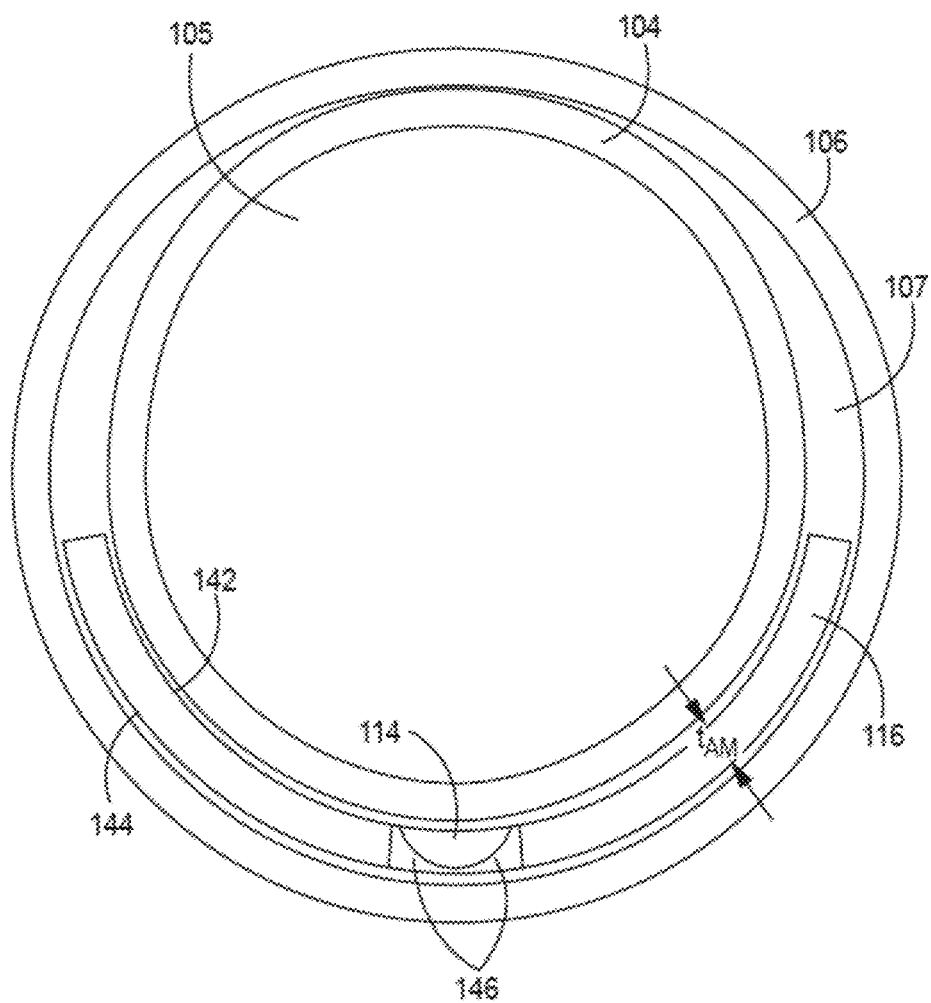
FIGS. 7A and 7B are conceptual cross-sectional views of examples of the catheter of FIGS. 1 and 2 taken along line 7-7 in FIG. 2.
Figure 7B:
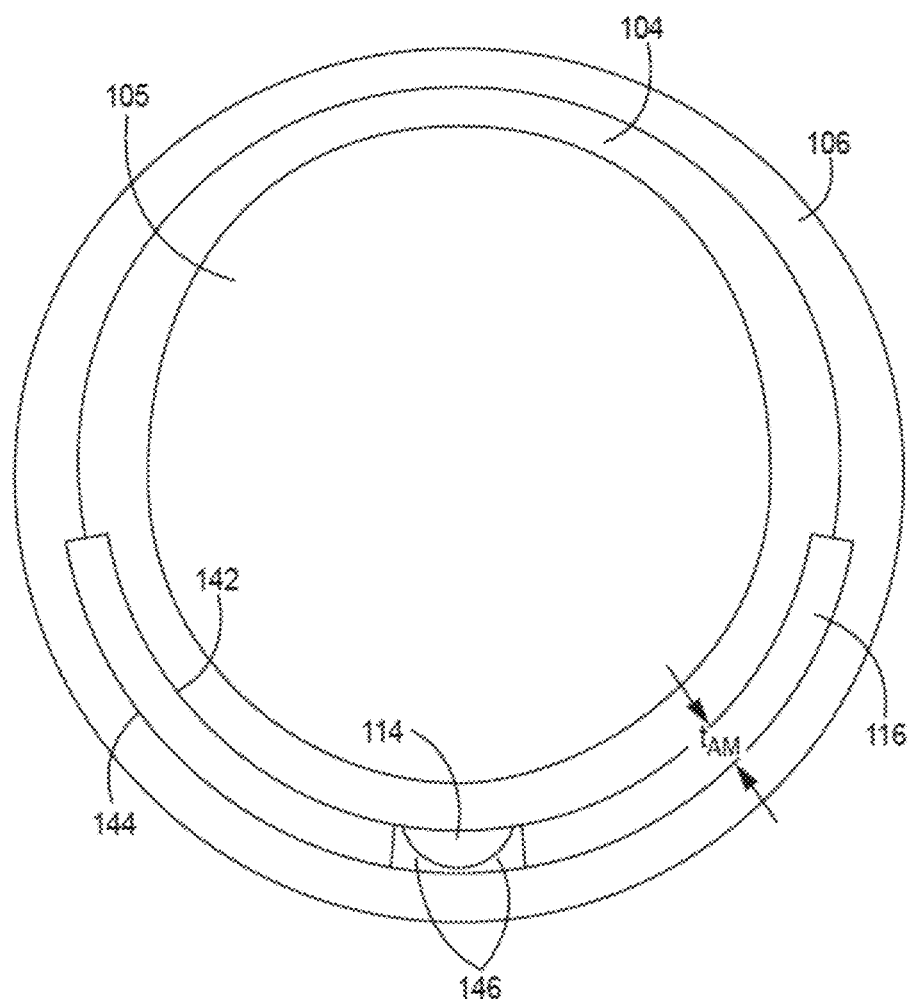
Figure 8A:
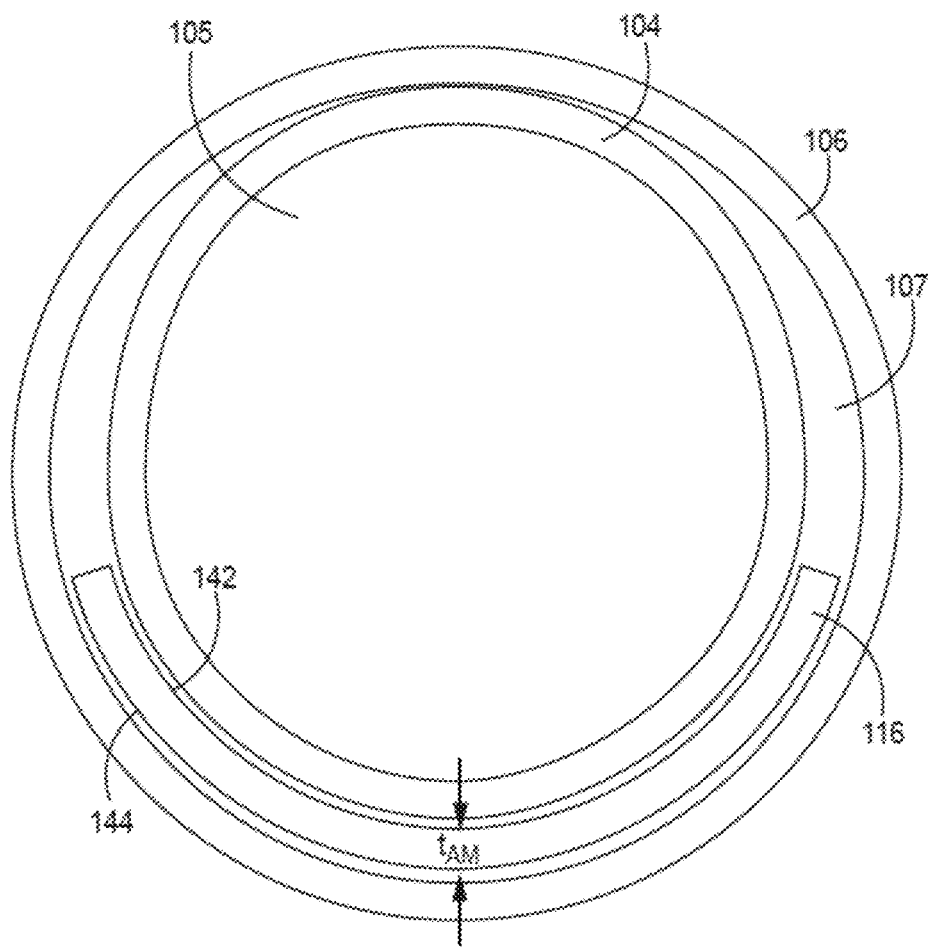
FIGS. 8A and 8B are conceptual cross-sectional views of examples of the catheter of FIGS. 1 and 2 taken along line 8-8 in FIG. 2.
Figure 8B:
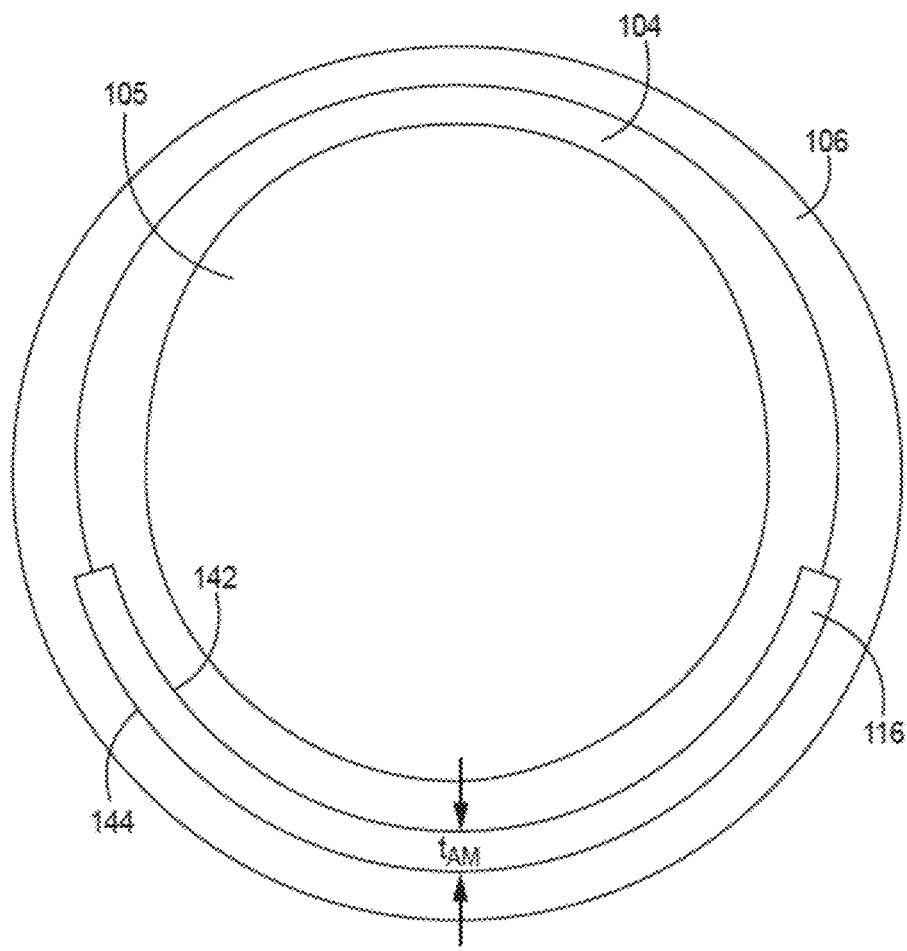

FIGS. 7A and 7B are conceptual cross-sectional views of examples of catheter 100 of FIGS. 1 and 2 taken along line 7-7 in FIG. 2, and FIGS. 8A and 8B are conceptual cross-sectional views of examples of catheter 100 of FIGS. 1 and 2 taken along line 8-8 in FIG. 2. FIGS. 7A and 8A are conceptual cross-sectional views of catheter 100 during assembly of elongate body 102, after anchor member 116 has been inserted and advanced between inner liner 104 and outer jacket 106. FIGS. 7B and 8B are a conceptual cross-sectional view of catheter 100 after assembly of catheter 100, after anchor member 116 has been inserted and advanced between inner liner 104 and outer jacket 106, as shown in FIGS. 7A and 8A, respectively, and after heat has been applied to inner liner 104 and outer jacket 106 to reflow material of inner liner 104 and outer jacket 106 around anchor member 116.

As shown in FIGS. 7A-8B, anchor member 116 may be positioned between outer jacket 106 and inner liner 104 such that anchor member 116 is positioned within outer jacket 106 and at least partially around an outer perimeter of inner liner 104. In some examples, anchor member 116 may extend about 140 degrees to about 160 degrees around the outer perimeter of inner liner 104. For example, a widest portion of anchor member 116, as shown in FIGS. 7A and 7B may extend about 140 degrees to about 160 degrees around the widest portion of inner liner 104. For example, in some examples, anchor member 116 may extend about 160 degrees around the outer perimeter of inner liner 104.

Anchor member 116 defines an inner surface 142 and an outer surface 144, and, in some examples, one or more of inner surface 142 and outer surface 144 may define a substantially semicircular surface but may, in some examples, include surface irregularities (e.g., waves, bumps, or other texturing). Anchor member 116 may have a thickness $t_{AM}$ measured in a direction perpendicular to longitudinal axis X of catheter 100. In some examples, thickness $t_{AM}$ may be about 50 micrometers thick to about 100 micrometers thick, such as about 76.2 micrometers thick or any other size suitable to fit between inner liner 104 and outer jacket 106 while also having suitable strength to secure push assembly 108 to elongate body 102. As shown in FIG. 6, welding material 146 may join elongate member 114 to anchor member 116, as describe in further detail below with respect to FIG. 15.

As shown in FIGS. 7B and 8B, in some examples, heat may be applied to inner liner 104 and/or outer jacket 106 to reflow material from inner liner 104 and/or outer jacket 106 around anchor member 116 to bond anchor member 116 between inner liner 104 and outer jacket 106. Although FIG. 7B shows reflow of material from both inner liner 104 and outer jacket 106, in some examples, heat may be applied to only one of inner liner 104 and outer jacket 106 and/or material from only one of inner liner 104 and outer jacket 106 may be reflowed around anchor member 116. Alternatively, or in addition to reflow, other methods may be used to bond anchor member 116 between inner liner 104 and outer jacket 106. For example, adhesives may be used. Bonding inner liner 104 and/or outer jacket 106 to anchor member 116 may improve the bond between elongate body 102 and push assembly 108 over methods wherein elongate member 114 is bonded directly to inner liner 104 and/or outer jacket 106, and may thus improve tensile strength, by providing greater surface area for bonding.

Figure 9:
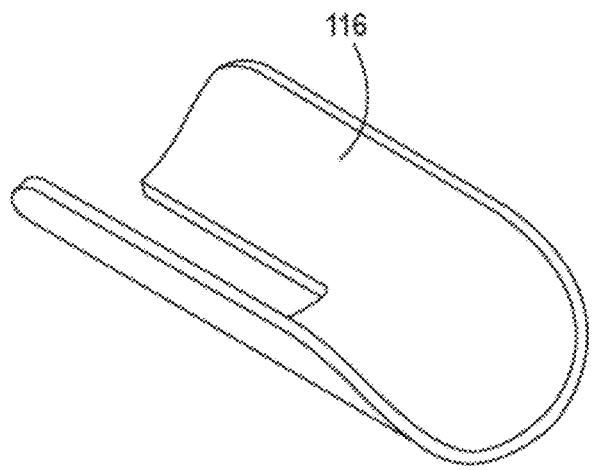
FIG. 9 is a conceptual perspective view of the anchor member of FIGS. 1, 2, 6, 7A, 7B, 8A, and 8B.
Figure 10A:
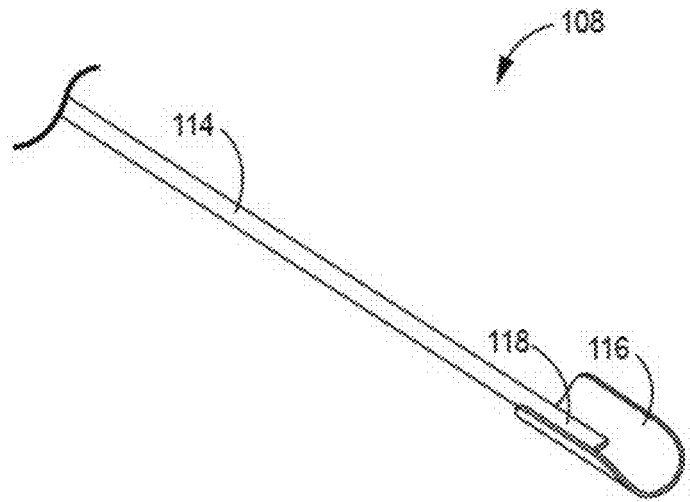
FIGS. 10A and 10B are conceptual perspective views of the push assembly of FIGS. 1, 2, 6, 7A, and 7B.
Figure 10B:
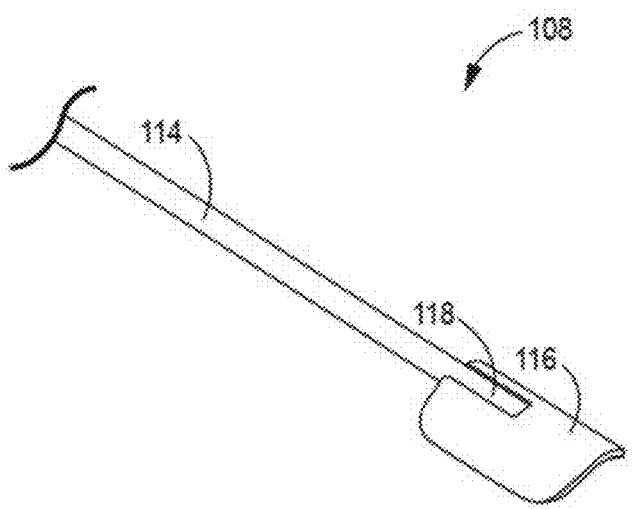

FIG. 9 is a conceptual perspective view of anchor member 116 of FIGS. 1, 2, 6, 7A, 7B, 8A, and 8B. FIGS. 10A and 10B are conceptual perspective views of push assembly 108 of FIGS. 1, 2, and 6. As shown in FIGS. 9, 10A, and 10B, anchor member 116 may define a partial-ring shape. As shown in FIGS. 10A and 10B, anchor member 116 may be secured to elongate member 114 to form push assembly 108. For example, anchor member 116 may be welded to distal end 118 of elongate member 114 as described in further detail below with reference to FIGS. 14 and 15. As another example, anchor member 116 may be adhered or otherwise mechanically connected to distal end 118 of elongate member 114.

In some examples, anchor member 116 may be formed of a radiopaque material such that anchor member 116 may serve as a radiopaque marker to indicate a location of entry port 109 to lumen 105 of elongate body 102. In other cases, a band may be added to anchor member 116 to serve as a marker. As discussed above, because anchor member 116 is not circular in cross-section, a radiopaque anchor member 116 may help indicate a rotational orientation of catheter 100 (e.g., a rotational orientation of entry port 109) within vasculature of a patient. In contrast, an anchor member having a circular cross-section would not indicate the rotational position of entry port 109 of catheter 100, as the rotational position of the anchor member within a medical image would not appear to change based on the rotational orientation of entry port 109 about longitudinal axis X.

Figure 11:
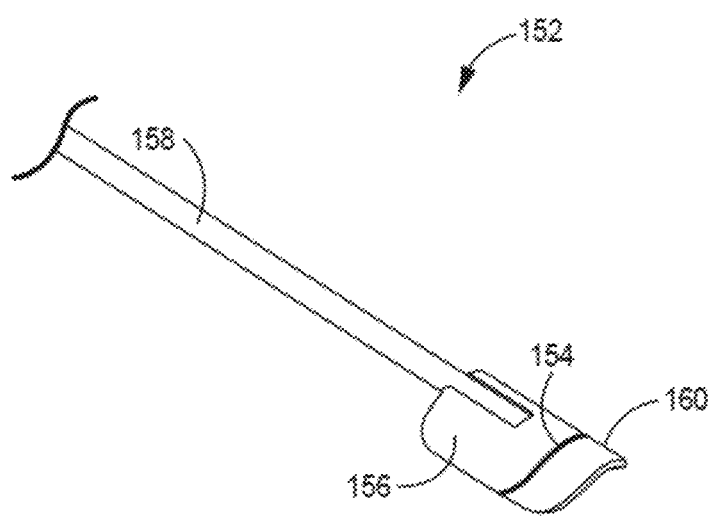
FIG. 11 is a conceptual perspective view of an example push assembly, such as the push assembly of FIGS. 1, 2, 10A and 10B, further including a radiopaque band.

FIG. 11 is a conceptual perspective view of an example push assembly 152, such as push assembly 108 of FIGS. 1, 2, 10A and 10B, further including a radiopaque band 154.

Push assembly 152 may include anchor member 156 and elongate member 158. In some examples, anchor member 156 may include one or more radiopaque bands 154 to facilitate visualization of anchor member 156.

Band 154 may be formed from a radiopaque material and can include, for example, a radiopaque marker band (e.g., one or more partial rings) attached to anchor member 158, e.g., by an adhesive or weld. In some examples, band 154 may include any suitable radiopaque material. In addition to, or instead of a radiopaque marker band, band 154 may include one or more grooves protruding from an outer surface 160 of anchor member 158 or defined by and recessed within outer surface 160 of anchor member 158. Although band 154 is shown along an outer diameter of anchor member 158, band 154 may include grooves including, for example, a series of tangential arcs along an inner diameter of anchor member 158 and may be formed from a radiopaque material, or may be filled with a radiopaque material in the case of recessed grooves, which may be visible within the patient with the aid of suitable medical imaging equipment. Band 154 may help a clinician determine an orientation and/or location of anchor member 158 and/or any suitable component of the device described herein.

Figure 12:
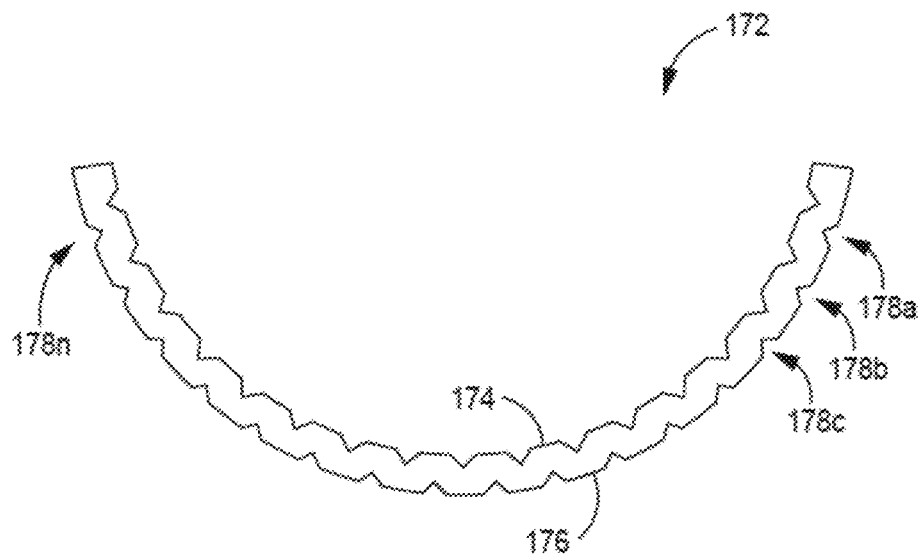
FIGS. 12 and 13 are conceptual cross-sectional views of example anchor members, such as the anchor member of FIGS. 1 and 2, with an inner surface and/or an outer surface defining a non-semicircular surface.
Figure 13:
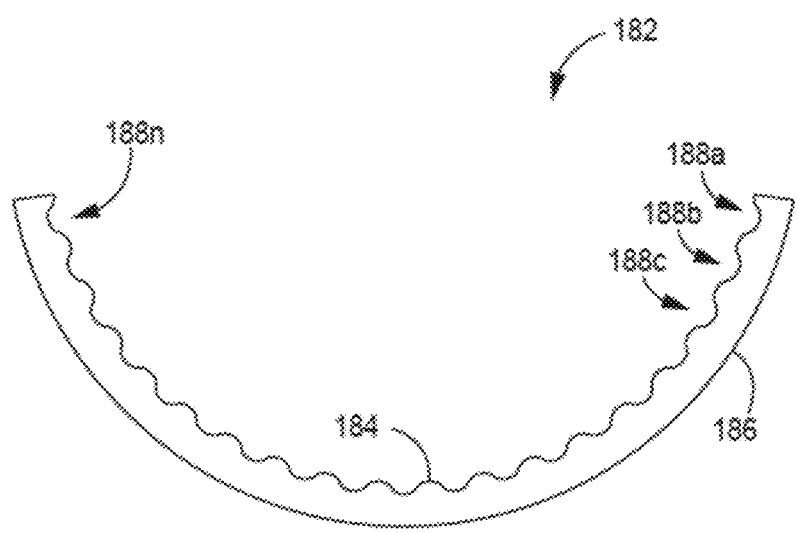

FIGS. 12 and 13 are conceptual cross-sectional views of example anchor members, such as anchor member 116 of FIGS. 1 and 2, with an inner and/or outer surface defining a non-semicircular surface. For example, as shown in FIG. 12, anchor member 172 may define inner surface 174 and outer surface 176, and one or more of inner surface 174 and outer surface 176 may define a non-semicircular surface. For example, outer surface 176 may define a plurality of notches 178a-178n. As another example, as shown in FIG. 13, anchor member 182 may define inner surface 184 and outer surface 186 and one or more of inner surface 184 and outer surface 186 may define a plurality of waves 188a-188n. In some examples, as in FIG. 12, both inner surface 174 and outer surface 176 may define a non-semicircular surface. In other examples, as in FIG. 12, only one of inner surface 174 and outer surface 176 may define a substantially non-semicircular surface.

Although FIGS. 12 and 13 show particular example anchor members 172 and 182 with non-semicircular and substantially semicircular surfaces, any suitable surfaces may be used according to particular needs. For example, an anchor member may define inner and outer surfaces both defining a plurality of waves. As another example, only one of an inner surface and an outer surface of an example anchor member may define a plurality of notches. In some examples, an anchor member may include one of an inner surface and an outer surface defining a plurality of notches and another of the inner surface and outer surface defining a plurality of waves. An anchor member may have any suitable combination of inner and outer surfaces according to particular needs.

In some examples, an anchor member with inner and/or outer surfaces defining non-semicircular surfaces may provide particular advantages. For example, such non-semicircular advantages may increase surface area of the surface(s) and thus improve bond between the anchor member and the inner liner, and/or the outer jacket. For example, reflow of inner liner and/or outer jacket material may bond with a greater surface area of the anchor member and may thus improve the bond between the inner liner and/or outer jacket and the anchor member.

Figure 14:
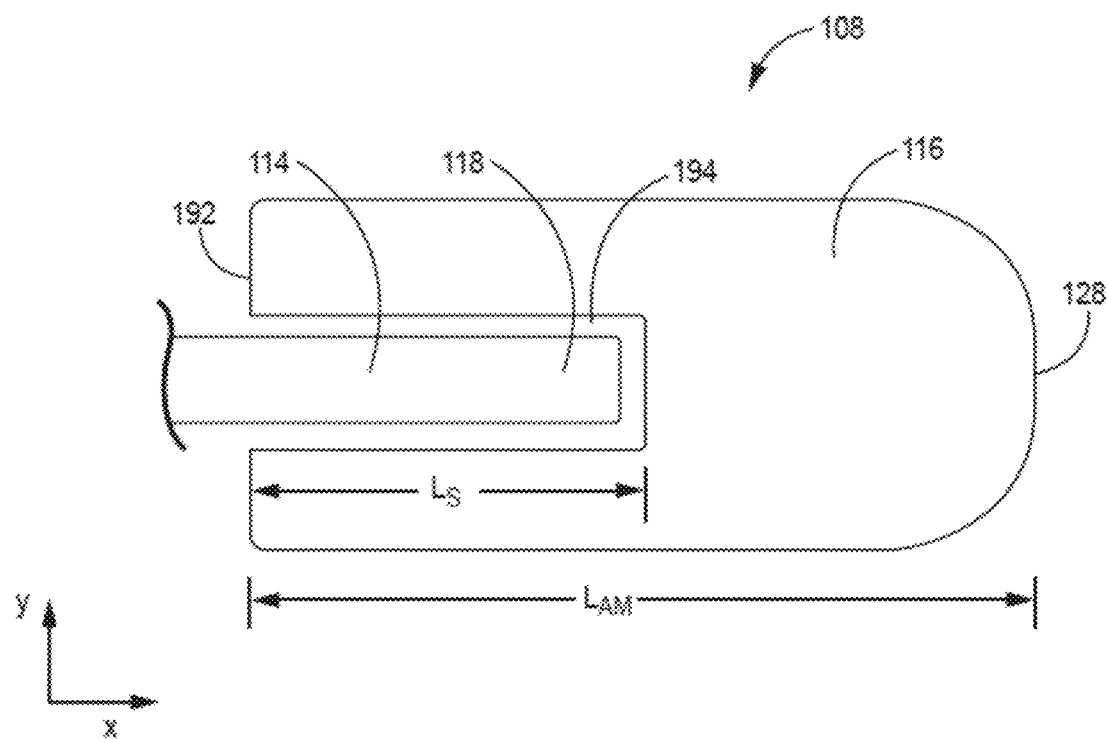
FIG. 14 is a conceptual side view of an example of the anchor member of the push assembly of FIGS. 2, 10A, and 10B and a distal portion of the elongate member of the push assembly of FIGS. 2, 10A, and 10B, before the anchor member and the elongate member are mechanically connected together to form the push assembly.
Figure 15:
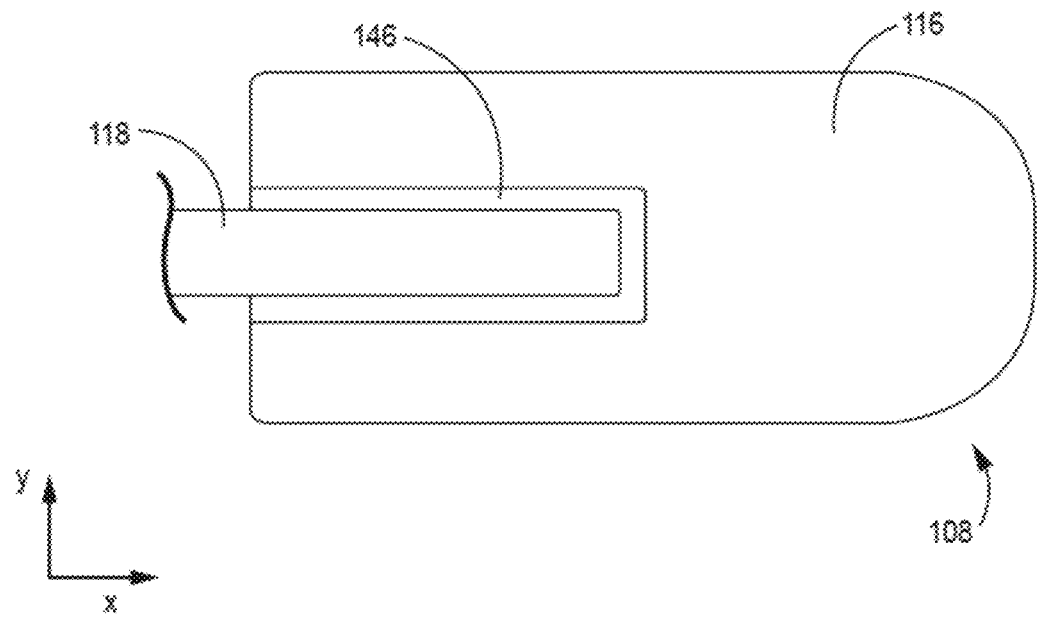
FIG. 15 is a conceptual side view of the push assembly of FIG. 14 after the anchor member and the elongate member are mechanically connected together to form the push assembly.

Anchor member 116 may be mechanically connected to elongate member 114 using any suitable technique, such as, but not limited to, welding, an adhesive, or mechanical fixation mechanism, such as a strap, or the like. FIG. 14 is a conceptual side view of an example of anchor member 116 of push assembly 108 of FIGS. 2, 10A, and 10B and a distal portion of elongate member 114 of the push assembly 108 of FIGS. 2, 10A, and 10B, before anchor member 116 and elongate member 114 are mechanically connected together to form push assembly 108. FIG. 15 is a conceptual side view of push assembly 108 of FIG. 14 after anchor member 116 and elongate member 114 are mechanically connected together to form push assembly 108.

As shown in FIG. 14, anchor member 116 may extend from a proximal end 192 to a distal end 128. Length $L_{AM}$ of anchor member 116 may be measured along axis X (where orthogonal x-y axes are shown in FIGS. 14 and 15 for ease of description only) from proximal end 192 to distal end 128 of anchor member 116. In some examples, length $L_{AM}$ of anchor member 116 is about 2 mm to about 5 mm, such as about 3 mm. Anchor 116 may have other lengths in other examples. Anchor member 116 may define a slot 194 extending from proximal end 192 towards distal end 128. In some examples, distal end 128 of elongate member 114 may be positioned at least partially within slot 194. In some examples, slot 194 has a length $L_S$ from about 25 percent to about 75 percent of a length $L_{AM}$ of anchor member 116. In some examples, length $L_S$ of slot 194 may be about 40 percent to about 60 percent of length $L_{AM}$ of anchor member 116. In some examples, anchor member 116 may be welded to elongate member 114. For example, as shown in FIG. 15, welding material 146 may be placed within slot 194 and between anchor member 116 and elongate member 114. In some examples, slot 194 may extend through the entire thickness $t_{AM}$ of anchor member 116. In other examples, slot 194 may extend only partially through thickness $t_{AM}$ of anchor member 116. Slot 194 may extend a thickness sufficient to receive distal end 118 of elongate member 114 and welding material 146.

Anchor member 116 defining a slot 194 within which distal end 118 of elongate member 114 and welding material 146 may be placed in order to bond distal end 118 of elongate member 114 to anchor member 116 may provide one or more advantages. For example, slot 194 may increase the surface area of the portions of elongate member 114 and anchor member 116 that are mechanically connected to each other, which may increase the strength of the mechanical connection between elongate member 114 and anchor member 116. As another example, slot 194 may provide for a lower radial profile of push assembly 108 compared to examples in which an anchor member does not include a slot or in which a slot is not wide enough for both distal end 118 of elongate member 114 and welding material 146 because distal end 118 and/or welding material 146 need not increase a radial profile of elongate body 102 and/or push assembly 108 by extending radially, inwardly or outwardly, from anchor member 116. This may also provide improved assembly of catheter 100 by providing a less bulky push assembly 108 that may be more easily inserted and advanced between inner liner 104 and outer jacket 106.

Figure 16:
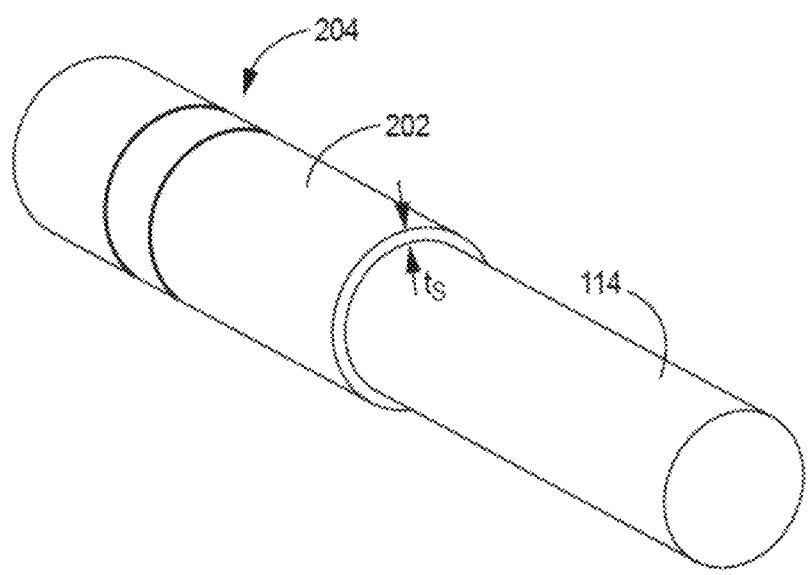
FIG. 16 is a conceptual perspective view of a portion of an example of the elongate member of FIGS. 1, 2, 10A, 10B, and 11.

FIG. 16 is a conceptual perspective view of a portion of an example elongate member 114 of FIGS. 1, 2, 10A, 10B, and 11. In some examples, a sleeve 202 may surround at least a portion of elongate member 114. In some examples, a sleeve 202 may surround at least a portion of elongate member 114 external to lumen 105 defined by elongate body. Sleeve 202 may include one or more layers of material configured to surround at least a portion of elongate member 114 and to distinguish elongate member 114 from other medical devices and/or to enable easier grip of elongate member 114.

In some examples, sleeve 202 may be textured such that it defines at least one textured surface, which may help a clinician grip sleeve 202 and/or sleeve 202 grip elongate member 114. For example, in some examples, sleeve 202 may be etched such that it defines at least one etched surface. As another example, sleeve 202 may define ridges, grooves, or the like on the surface facing outward (the surface that a clinician would grip when engaging sleeve 202), and/or on the surface facing elongate member 114.

In addition to, or instead of, aiding a clinician's handling of elongate member 114, in some examples, sleeve 202 may provide one or more visible indicia that help differentiate elongate member 114 from other medical devices. For example, sleeve 202 may be a different color than at least one of elongate member 114, inner liner 104, and outer jacket 106. In addition, or instead, sleeve 202 may include one or more visible and/or tactile bands 204. In some examples, bands 204 may include a partial cut around a perimeter of sleeve 202. In some examples, the partial cut may extend only partially through a radial thickness $t_S$ of sleeve 202. In some examples, the partial cut may extend 360 degrees around a perimeter of sleeve 202. Bands 204 may include a double-stripe mark. Bands 204 may include a marker with any suitable visual characteristics, such as, but not limited to, a particular color(s), visible pattern(s), and/or texture(s).

Sleeve 202 may provide particular advantages. For example, sleeve 202 including a textured surface, having a distinct color, having bands 204 and/or or other visually distinct indicium or indicia may help to tactilely and/or visually distinguish elongate member 114 from other components including, for example, a guidewire or other catheters or devices used with catheter 100 such that a user may more easily distinguish it from other components. For example, without sleeve 202, elongate member 114 may look and/or feel like a guidewire and may be difficult to identify as being a part of push assembly 108.

Figure 17:
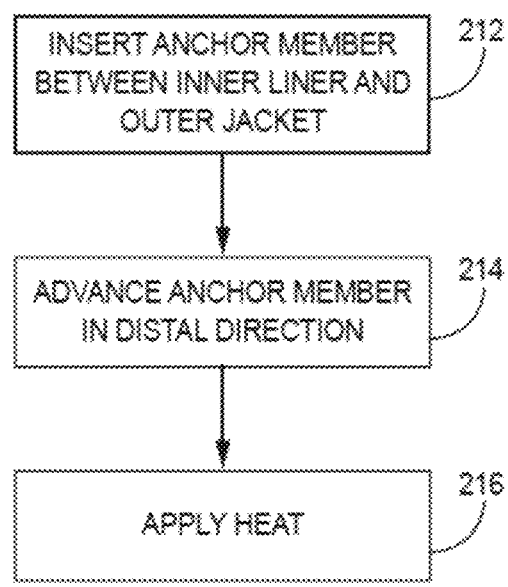
FIG. 17 is a flowchart illustrating an example method of assembling the example catheter shown in FIGS. 1 and 2.

FIG. 17 is a flowchart illustrating an example method including the various stages of assembly of example catheter 100 shown in FIGS. 1 and 2. In accordance with this method of assembly, anchor member 116 of push assembly 108 is inserted between inner liner 104 and outer jacket 106 of catheter 100 such that, after insertion, anchor member 116 extends only partially around an outer perimeter of inner liner 104 (212). In some examples, anchor member 116 is advanced between inner liner 104 and outer jacket 106 in a distal direction (214). In some examples, anchor member 116 may be advanced between inner liner 104 and outer jacket 106 in a distal direction until proximal end 192 of anchor member 116 is aligned with proximal end 138 of entry port 109. In other examples, anchor member 116 may be advanced between inner liner 104 and outer jacket 106 in a distal direction until distal end 128 of anchor member 116 is aligned with distal end 140 of entry port 109. Anchor member 116 may be advanced to any suitable position between inner liner 104 and outer jacket 106 according to particular needs.

After insertion and advancement of anchor member 116, distal to proximal end 10 of elongate body 102, a portion of push assembly 108, including anchor member 116, is positioned between adjacent portions inner liner 104 and outer jacket 106 and, proximal end 10 of elongate body 102, a portion of push assembly 108 is positioned outside of outer jacket 106 and inner liner 104.

In some examples, heat may be applied to inner liner 104 and/or outer jacket 106 to reflow material around anchor member 116 (214).

In some examples, a method of assembly may further include abrasive processing of elongate member 114 to form a taper, such as the D-shaped taper illustrated in FIGS. 4 and 5. The abrasive processing may include, for example, grinding, sanding, or grit blasting at least a portion of elongate member 114 to remove material.

In some examples, a method of assembly may further include coupling anchor member 116 to elongate member 114. For example, anchor member 116 may be coupled to elongate member 114 before insertion of anchor member 116 between inner liner 104 and outer jacket 106 of catheter 100. In some examples, coupling anchor member 116 to elongate member 114 may include positioning distal end 118 of elongate member 114 at least partially within slot 194 of anchor member 116. In some examples, coupling anchor member 116 to elongate member 114 may include welding anchor member 116 to elongate member 114. In some examples, welding anchor member 116 to elongate member 114 may include placing welding material 146 within slot 194 and between anchor member 116 and elongate member 114.

In some examples, the method may further include positioning reinforcement member 126 between at least a portion of inner liner 104 and at least a portion of outer jacket 106. In some examples, the method may include positioning distal end 128 of anchor member 116 proximal to reinforcement member 126. In some examples, the method may include positioning distal end 128 of anchor member 116 such that it abuts proximal end 130 of reinforcement member 126. In some examples, the method may include positioning sleeve 202 around at least a portion of elongate member 114.

In some examples, a catheter may include a distal tip portion configured to reduce impact force between a distal tip of the catheter and tissue of a patient during as the catheter is advance through vasculature of a patient. The distal tip portion may include a construction that reduces an effective durometer of the distal tip portion compared to a more proximal portion of the catheter. For example, the distal tip portion may include a tip outer jacket that includes a material or mixture of materials that has a lower durometer than an outer jacket of a more proximal portion of the catheter. As another example, an inner liner may end proximal of the distal tip, reducing an effective durometer of the distal tip portion.

Figure 18:
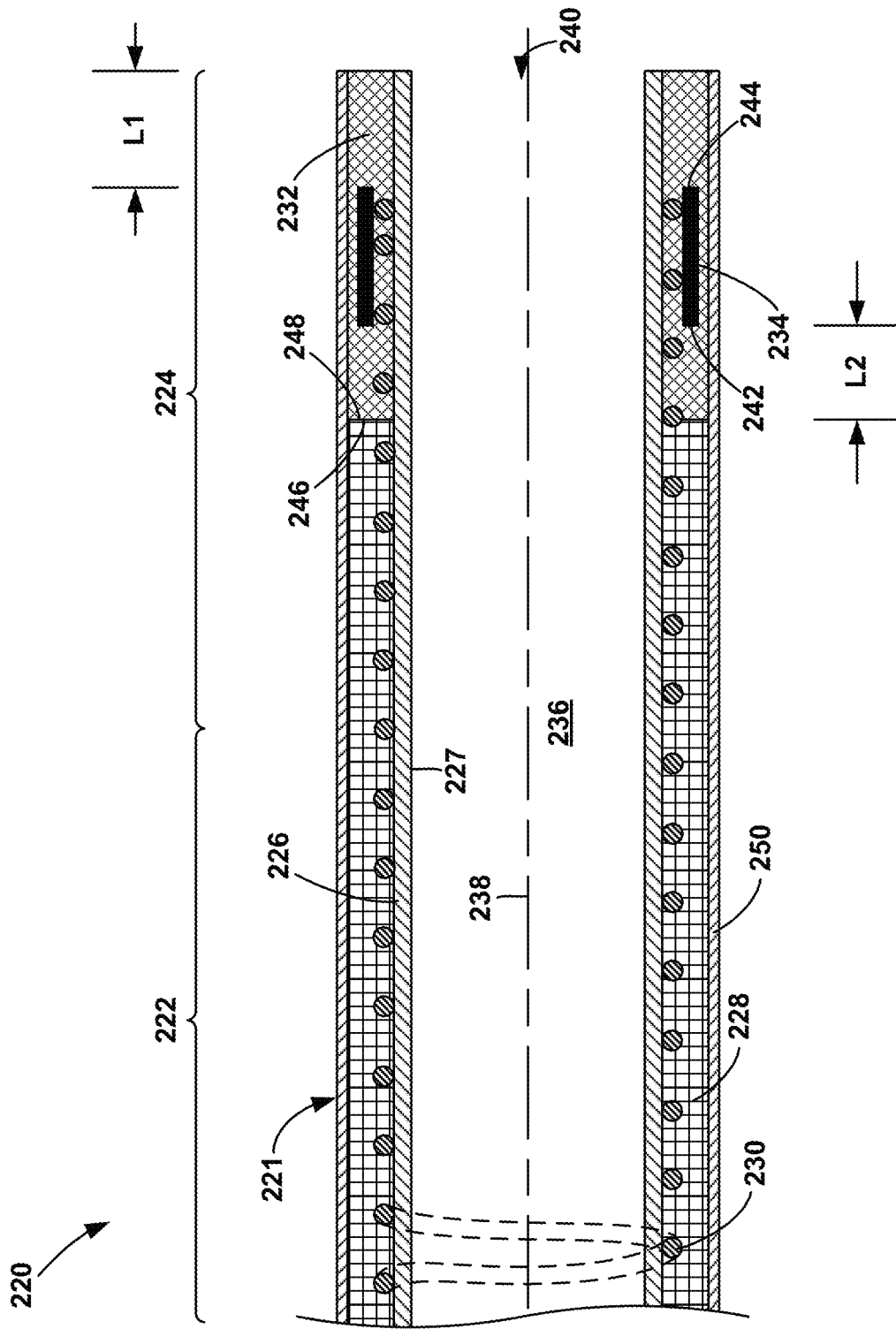
FIGS. 18-23 are conceptual side cross-sectional views of a distal tip portion of example catheters.

FIGS. 18-23 are conceptual side cross-sectional views of a distal tip portion of example catheters that include a distal tip portion configured to reduce impact force between a distal tip of the catheter and tissue of a patient during as the catheter is advance through vasculature of a patient. FIG. 18 illustrates part of a catheter 220 that includes an elongate body 221 including a proximal portion 222 and a distal tip portion 224. Catheter 220 may be an example of any of the other catheters described herein, such as catheter 100. As such, a portion of catheter 220 not shown in FIG. 18 may include a push assembly (like push assembly 108) that includes an elongate push member joined to elongate body 221 at or near a proximal end of elongate body 221.

Elongate body 221 includes proximal portion 222 and distal tip portion 224. Proximal portion 222 is proximal of distal tip portion 224 and may extend to a proximal end of elongate body 221. Proximal portion 222 includes a proximal portion of an inner liner 226, a proximal portion of an outer jacket 228, and a proximal portion of a reinforcement member 230.

Inner liner 226 defines a lumen 236 that extends from adjacent to or at a proximal end of elongate body 221 to adjacent to or at distal end 240 of elongate body 221. Lumen 236 enables introduction of a medical device (e.g., a catheter, guidewire, filter, stent delivery system, and the like), therapeutic agent, or other element into vasculature or other tissue sites of a patient.

Inner liner 226 may be formed from any suitable material, such as, but not limited to a fluoropolymer, such as polytetrafluorethylene (PTFE), a polyolefin, such as high density polyethylene (HDPE), or the like. In some examples, inner liner 226 may include a lubricious or hydrophilic coating o inner surface 227. In some examples, inner liner 226 may include multiple layers, such as a radially inner layer including a fluoropolymer or polyolefin and a radially outer layer that increases adhesion to outer jacket 228. The radially outer layer may include any suitable adhesion-increasing polymer, such as, for example, a polyamide, a polyimide, or a poly(ether-block-amide). In some implementations, the radially inner layer may constitute approximately 75% of the thickness of inner liner 226 and the radially outer layer may constitute approximately 25% of the thickness of inner liner 226.

Outer jacket 228 may include any suitable material, such as any suitable polymer. In some examples, outer jacket 228 may include a polyamide, a polyimide, or a poly(ether-block-amide). The polymer may be selected to have tensile properties that facilitate force transfer axially along elongate body 221 to enable pushing of catheter 220 and advancing catheter 220 through vasculature of a patient, through lumen 111 of outer catheter 110 (FIG. 1), or the like. For example, outer jacket 228 may include a mixture of a first poly(ether-block-amide) available under the trade designation PEBAX® 5533 (having a Shore D hardness of about 54) from Arkema Group, Colombes, France and a second poly(ether-block-amide) available under the trade designation PEBAX® 6333 from Arkema. PEBAX® 5522 has a durometer or Shore D hardness of about 54 and PEBAX® 6333 has a durometer or Shore D hardness of about 64. Thus, a mixture or blend of PEBAX® 5533 and PEBAX® 6333 may have a durometer or Shore D hardness between about 54 and 64, depending on the relative amounts of the first and second poly(ether-block-amide).

In some examples, elongate body 221 also includes a reinforcement member 230 radially outward from inner liner 226 and radially inward from or within outer jacket 228. Reinforcement member 230 may be any suitable structure configured to provide structural support to elongate body 221 and, in some examples, increase the structural integrity of elongate body 221, e.g., to facilitate force transfer axially along elongate body 221 to enable pushing of catheter 220 and advancing catheter 220 through vasculature of a patient, through lumen 111 of outer catheter 110 (FIG. 1), or the like. For example, reinforcement member 221 may comprise a metal coil, a metal braid, or a combination thereof. Reinforcement member 230 may be between inner liner 226 and outer jacket 228 or may be embedded within outer jacket 228, as shown in FIG. 18.

In the example shown in FIG. 18, each of inner liner 226, outer jacket 228, and reinforcement member 230 extend into distal tip portion 224 of elongate body 221. As shown in FIG. 18, in some examples, outer jacket 228 ends at a distal outer jacket end 246 that is proximal of the distal tip 240 of elongate body 221. Distal of distal outer jacket end 246 and laterally adjacent to outer jacket 228, elongate body 221 includes a tip outer jacket 232. In some examples, a proximal tip outer jacket end 248 of tip outer jacket 232 laterally abuts (contacts) distal outer jacket end 246. In other examples, proximal tip outer jacket end 248 is bonded to distal outer jacket end 246, e.g., using diffusion bonding, polymer welding, or the like.

Tip outer jacket 232 may include any suitable material, such as any suitable polymer. In some examples, tip outer jacket 232 may include a polyamide, a polyimide, or a poly(ether-block-amide). The polymer may be selected to have a durometer or hardness less than the durometer or hardness of outer jacket 228. For example, tip outer jacket 232 may include a poly(ether-block-amide) available under the trade designation PEBAX® 2533 from Arkema Group. PEBAX® 2533 has a Shore D hardness of about 27. Due to the lower durometer or hardness of tip outer jacket 232 compared to outer jacket 228, distal tip portion 224 may reduce force transmission from catheter 220 to tissue upon contact between distal tip 240 and tissue compared to a catheter in which outer jacket 228 extends to distal tip 240. For example, distal tip portion 224 may more easily compress or deflect due to its lower hardness, which reduces force transmission to tissue. This may result in distal tip portion 224 being more atraumatic to tissue.

In some examples, elongate body 221 may include an optional hydrophilic coating 250 on outer surfaces of outer jacket 228 and tip outer jacket 232. Hydrophilic coating 250 may include, for example, a hydrogel or other hydrophilic material.

As shown in FIG. 18, a marker band 234 is embedded in tip outer jacket 232, and tip outer jacket 232 extends both proximal and distal to marker band 234. Marker band 234 may include a cylinder or partial cylinder of a radiopaque material, such as a radiopaque metal or alloy. Example radiopaque metals or alloys include platinum iridium (PtIr), cobalt chromium (CoCr), and the like. Marker band 234 facilitates imaging of the distal end of catheter 220, but also may increase the hardness of catheter 220 at the axial position of marker band 234. As such, by having tip outer jacket 232 extend both proximal and distal to marker band 234, the reduced durometer or hardness of tip outer jacket 232 may facilitate bending or deflection of catheter 220 both proximal and distal to marker band 234. This also contributes to distal tip portion 224 being more atraumatic to tissue.

In some examples, marker band 234 defines an axial length (between marker band proximal end 242 and marker band distal end 244) of between about 0.5 mm and about 1.2 mm, such as between about 0.8 mm and about 1.0 mm. Tip outer jacket 232 may extend a length L1 beyond (distal to) marker band distal end 244. Length L1 may be between about 1.5 mm and about 3.0 mm, such as between about 1.5 mm and about 2.5 mm, or about 2.2±0.5 mm.

Tip outer jacket 232 may extend a length L2 proximal to marker band proximal end 242. Length L2 may be between about 1.5 mm and about 3.0 mm, such as between about 1.5 mm and about 2.5 mm, or about 2.2±0.7 mm.

Figure 19:
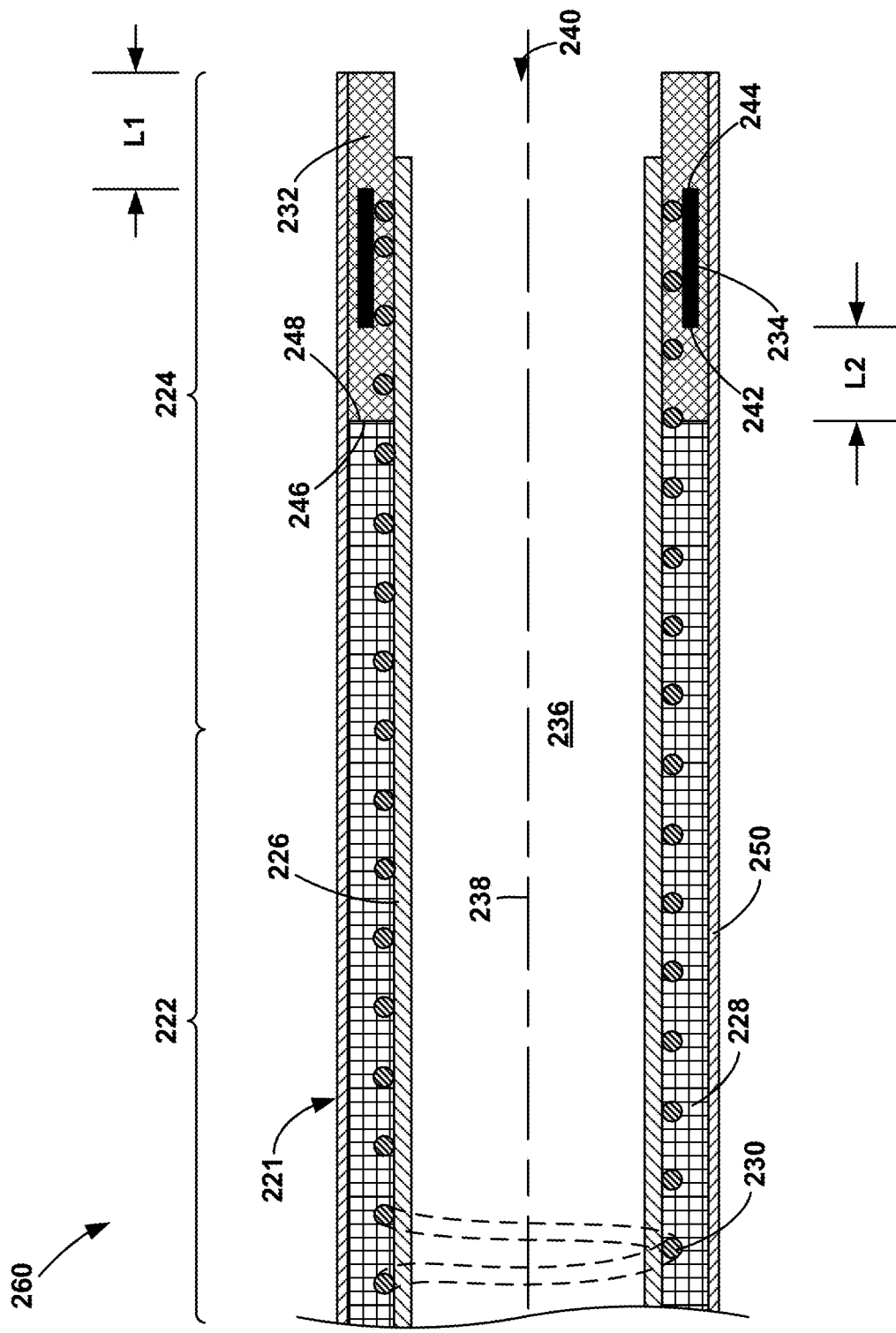
Figure 20:
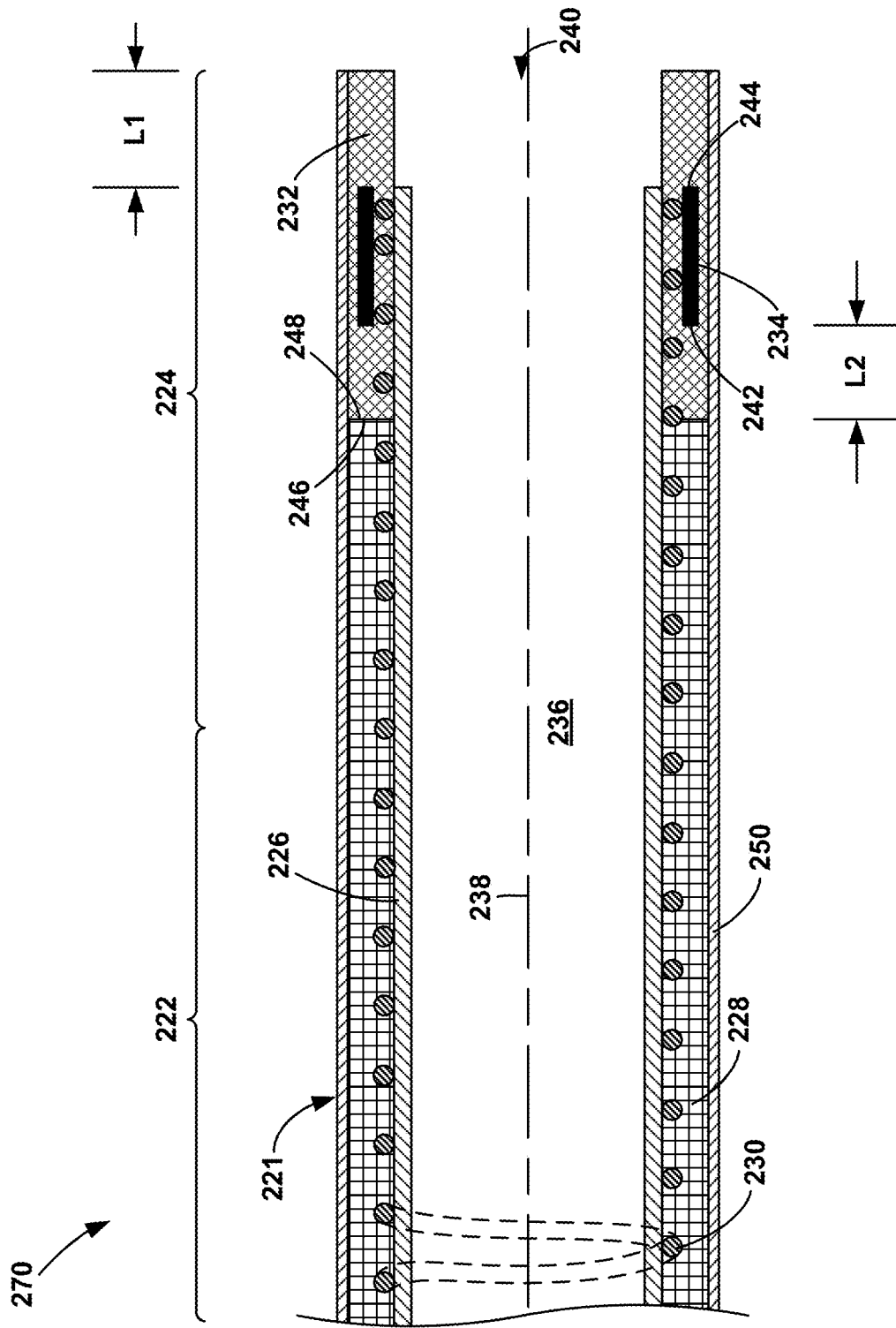

In the example shown in FIG. 18, inner liner 226 extends to distal tip 240 of elongate body 221. In other examples, inner liner 226 may terminate proximal to distal tip 240. By terminating inner liner 226 proximal to distal tip 240, the durometer or hardness of the distal-most portion of distal tip portion 224 may be further reduced, further reducing force transmission from catheter 220 to tissue in the event of contact. For example, as shown in FIG. 19, a catheter 260 may include an inner liner 226 that ends distal to marker band distal end 244 and proximal to distal tip 240. As another example, as shown in FIG. 20, a catheter 270 may include an inner liner 226 that ends at about marker band distal end 244 (e.g., is aligned with marker band distal end 244 to the extent permitted by manufacturing tolerances or is within about 0.1 mm of marker band distal end 244) and proximal to distal tip 240. Inner liner 232 may extend distal of a distal end of reinforcement member 230 to reduce a likelihood of reinforcement member 230 separating from other components of catheter 220.

Figure 21:
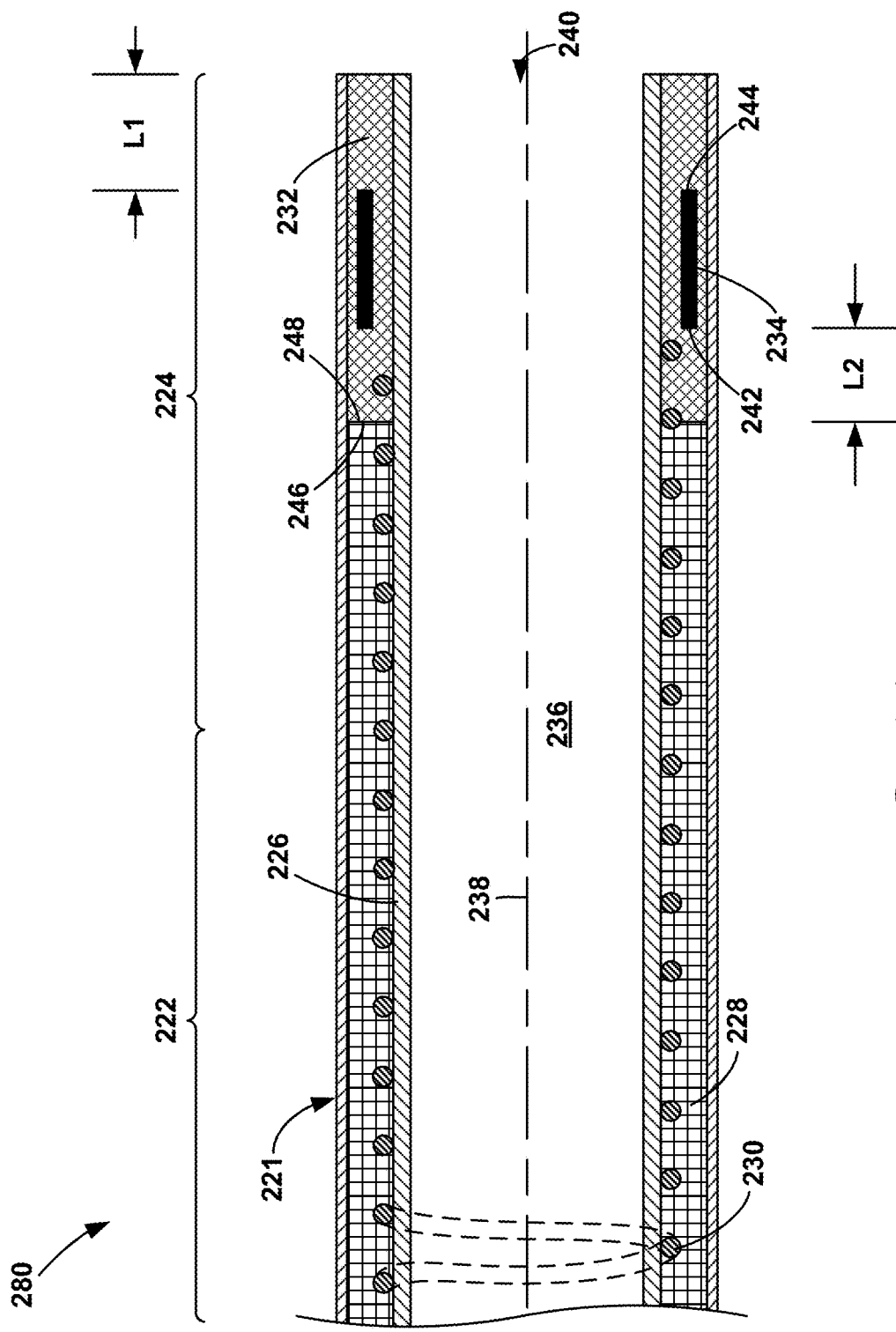
Figure 22:
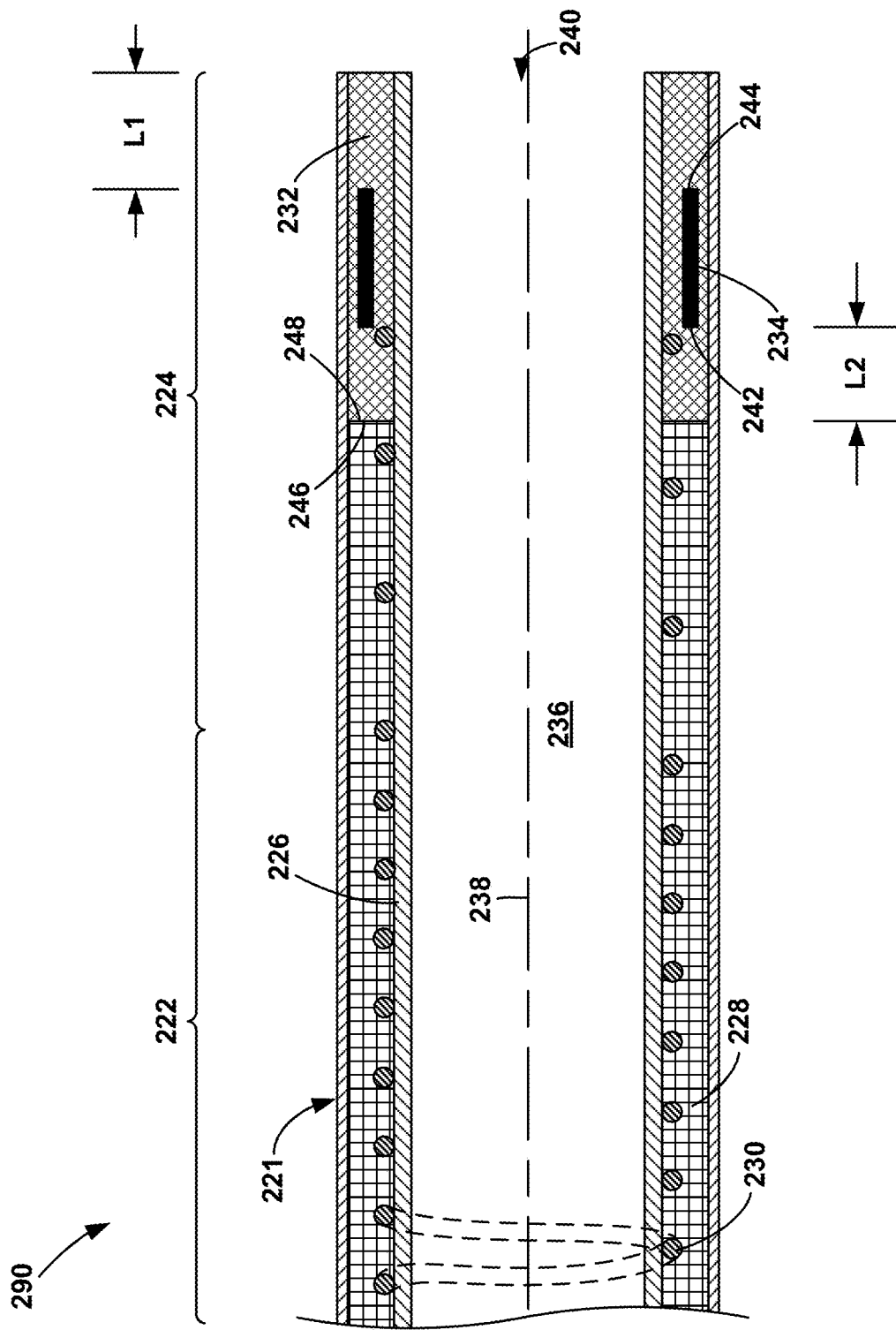

In the example shown in FIG. 18, reinforcement member 230 extends under and overlaps marker band 234 such that marker band 234 helps maintain the position of the distal end of reinforcement member 230 within catheter 220. In other examples, a catheter 280 may include a reinforcement member 230 that ends proximal of marker band proximal end 242, as shown in FIG. 21, or a catheter 290 may include a reinforcement member 230 that ends substantially aligned with marker band proximal end 242, as shown in FIG. 22. Further, reinforcement member 230 may include substantially constant spacing (or pitch) between adjacent turns of the reinforcement elements (e.g., coil windings in a coil or filament windings in a braid), as shown in FIGS. 18-21. In other examples, reinforcement member 230 may include a changing spacing (or pitch) between adjacent turns of the reinforcement elements. For example, as shown in FIG. 22, a catheter 290 may include a reinforcement member 230 that includes a first spacing or pitch between adjacent turns of the reinforcement elements in proximal portion 222 and a second spacing or pitch between adjacent turns of the reinforcement elements in distal tip portion 224. The second spacing or pitch may be greater than the first spacing or pitch, as shown in FIG. 22, or may be less than the first spacing or pitch. Changing the spacing or pitch of reinforcement member 230 from proximal portion 222 to distal tip portion 224 may provide further control to the hardness of distal tip portion 224 relative to proximal portion 222.

Figure 23:
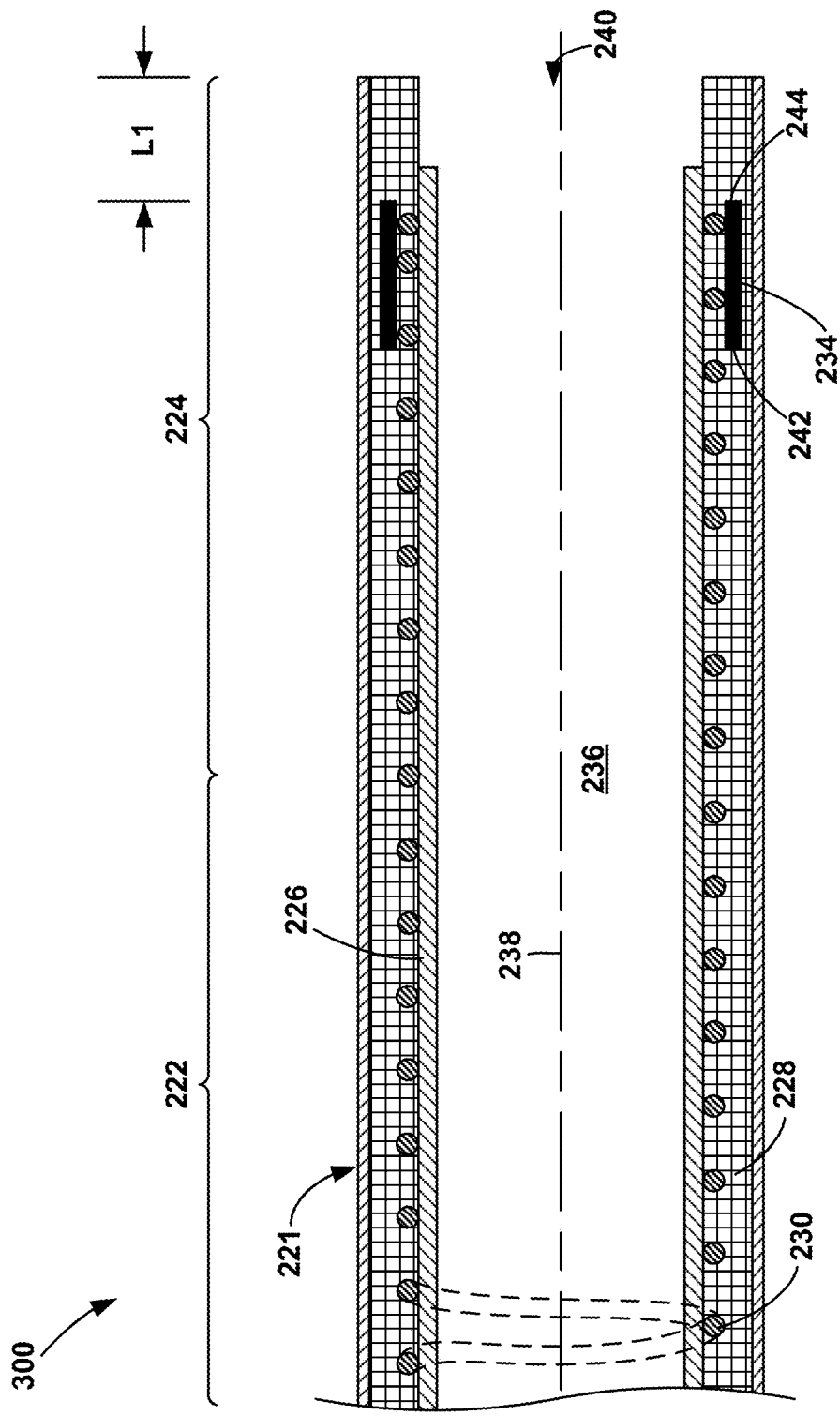

In some implementations, a catheter may not include a separate tip outer layer, and a configuration of other structural components of the catheter may be designed to reduce impact force between a distal tip of the catheter and tissue of a patient during as the catheter is advance through vasculature of a patient. For example, FIG. 23 is a conceptual cross-sectional diagram of an example catheter 300 in which outer jacket 228 extends to distal tip 240 of elongate body 221. In the example of FIG. 23, inner liner 226 ends distal of marker band distal end 244 and proximal to distal tip 240 of elongate body 221. In this way, a distal-most part of distal tip portion 224 had a lower hardness or durometer due to the omission of inner liner 226. Inner liner 226 may end at any position between marker band distal end 244 and proximal to distal tip 240 of elongate body 221, e.g., the position shown in FIG. 20. The structural features illustrated in FIG. 23 for catheter 300 may be combined with other features illustrated in FIGS. 18-22, as will be apparent to a person having ordinary skill in the art.

Example

Figure 24:
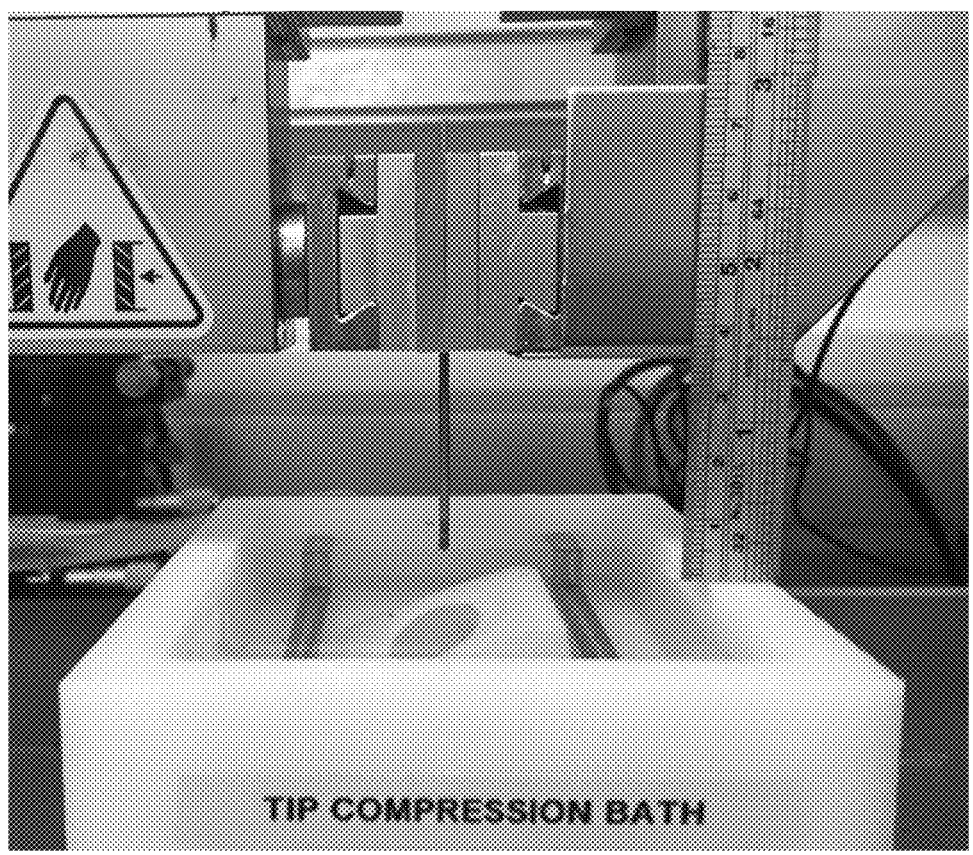
FIG. 24 is an image of an example tensile testing machine used to measure tip compression force.

A vertically-oriented tensile test machine available from ZwickRoell USA, Kennesaw, Georgia was modified by removing the bottom grip. A compression water bath was secured on the base of the tensile test machine with the top grip centered directly over a 45-degree angled test surface, as shown in FIG. 24. The distance between the bottom of the top grip and the top of the compression water bath was about 35 mm.

The tip compression bath was filled with water and water circulated between the tip compression bath and a heater to heat the water to a temperature of about 37±2° C.

For each catheter tested, about 70 mm of the distal-most portion was separated from the catheter. A support pin was inserted in the lumen of the distal-most portion and extended about 4 mm past the proximal end of the distal-most portion. The distal-most portion was placed in the groove of the top grip and the distal end of the distal-most portion extended about 35 mm from the bottom of the top grip.

Figure 25:
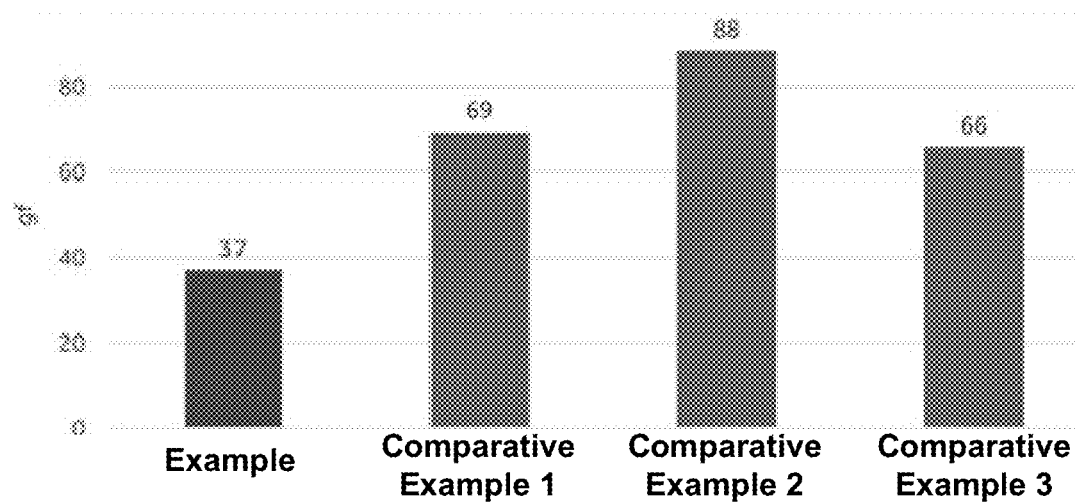
FIG. 25 is a plot of tip compression force measured in grams-force for an example catheter constructed in accordance with this disclosure and three comparative examples.

To test tip compression force, the tensile test machine was programmed to advance the catheter vertically a total of 2 mm after detecting contact of the distal tip with the test surface. The force output was recorded. FIG. 25 is a plot of tip compression force measured in grams-force for an example catheter constructed in accordance with this disclosure and three comparative examples. As shown in FIG. 25, the tip compression force is significantly lower for the example catheter constructed in accordance with this disclosure.

Various examples have been described. These and other examples are within the scope of the following claims.

What is claimed is:

1. A catheter comprising:
   an elongate body comprising:
   a proximal portion including a proximal end of the elongate body; and
   a distal tip portion, wherein the distal tip portion comprises:
   an inner liner;
   a reinforcement member surrounding the inner liner;
   at least one marker band surrounding the inner liner, each marker band of the at least one marker band extending from a respective marker band proximal end to a respective marker band distal end;
   an outer jacket surrounding a first portion of the inner liner and ending proximal of a proximal-most marker band proximal end; and
   a tip outer jacket surrounding a second portion of the inner liner and the at least one marker band, including proximal and distal ends of the at least one marker band, wherein the tip outer jacket extends distally past a distal-most marker band distal end to a distal tip of the elongate body, wherein a proximal end of the tip outer jacket is laterally adjacent to a distal end of the outer jacket, wherein the tip outer jacket exhibits a different durometer than the outer jacket; and
   an elongate push member, wherein the elongate push member is mechanically coupled to the proximal end of the elongate body, wherein a distalmost edge of the elongate push member contacts a proximal end of the reinforcement member, and wherein the elongate push member has a lower profile than the elongate body.

2. The catheter of claim 1, wherein the elongate body defines at least one lumen extending from adjacent to or at the proximal end of the elongate body to adjacent to or at the distal tip.

3. The catheter of claim 1, wherein the inner liner extends to the distal tip of the elongate body.

4. The catheter of claim 1, wherein the inner liner ends distal to the marker band distal end and proximal to the distal tip.

5. The catheter of claim 1, wherein the tip outer jacket extends about 1.5 mm to about 3.0 mm distal of the marker band distal end.

6. The catheter of claim 1, wherein the tip outer jacket extends proximal to the proximal-most marker band proximal end.

7. The catheter of claim 1, wherein the tip outer jacket extends about 1.5 mm to about 3.0 mm proximal of the marker band proximal end.

8. The catheter of claim 1, wherein the at least one marker band has a length of about 0.5 mm to about 1.2 mm between the marker band proximal end and the marker band distal end.

9. The catheter of claim 1, wherein the proximal end of the tip outer jacket laterally abuts the distal end of the outer jacket.

10. The catheter of claim 1, wherein the proximal end of the tip outer jacket is bonded to the distal end of the outer jacket.

11. The catheter of claim 1, wherein the tip outer jacket exhibits a lower durometer than the outer jacket.

12. The catheter of claim 1, wherein the reinforcement member does not extend distally past the marker band distal end.

13. The catheter of claim 12, wherein a distal end of the reinforcement member overlaps the marker band.

14. The catheter of claim 1, wherein the reinforcement member comprises a coil, wherein coil defines a first pitch in the proximal portion, wherein the coil defines a second pitch in the distal tip portion, and wherein the second pitch is greater than the first pitch.

15. The catheter of claim 1, wherein the outer jacket comprises a first poly (ether-block-amide), and wherein the tip outer jacket comprises a second, different poly (ether-block-amide).

16. The catheter of claim 1, wherein the outer jacket comprises a mixture of a first poly (ether-block-amide) and a second poly (ether-block-amide), and wherein the tip outer jacket comprises a third, different poly (ether-block-amide).

17. The catheter of claim 1, wherein a portion of the elongate push member is positioned between the inner liner and the outer jacket.

18. A catheter comprising:
   an elongate body comprising:
   a proximal portion including a proximal end of the elongate body; and
   a distal tip portion, wherein the distal tip portion comprises:
   an inner liner;
   a reinforcement member surrounding the inner liner;
   at least one marker band surrounding the inner liner, each marker band of the at least one marker band extending from a respective marker band proximal end to a respective marker band distal end;
   an outer jacket surrounding a first portion of the inner liner and ending proximal of a proximal-most marker band proximal end; and
   a tip outer jacket surrounding a second portion of the inner liner and the at least one marker band, including proximal and distal ends of the at least one marker band, wherein the tip outer jacket extends distally past a distal-most marker band distal end, wherein a proximal end of the tip outer jacket is laterally adjacent to a distal end of the outer jacket, wherein the tip outer jacket exhibits a different durometer than the outer jacket; and
   an elongate push member comprising an elongate member and an anchor member positioned at a distal end of the elongate member, wherein the elongate push member is mechanically coupled to the proximal end of the elongate body, and wherein a distalmost edge of the anchor member contacts the reinforcement member.

19. The catheter of claim 18, wherein a portion of the elongate push member is positioned between the inner liner and the outer jacket.

20. A catheter comprising:
   an elongate body comprising:
   a proximal portion including a proximal end of the elongate body; and
   a distal tip portion, wherein the distal tip portion comprises:
   an inner liner;
   a reinforcement member surrounding the inner liner;
   at least one marker band surrounding the inner liner, each marker band of the at least one marker band extending from a respective marker band proximal end to a respective marker band distal end;
   an outer jacket surrounding a first portion of the inner liner and ending proximal of a proximal-most marker band proximal end; and
   a tip outer jacket surrounding a second portion of the inner liner and the at least one marker band, including proximal and distal ends of the at least one marker band, wherein the tip outer jacket extends distally past a distal-most marker band distal end to a distal tip of the elongate body, wherein a proximal end of the tip outer jacket is laterally adjacent to a distal end of the outer jacket, wherein the tip outer jacket exhibits a different durometer than the outer jacket; and an elongate push member, wherein the elongate push member is mechanically coupled to the proximal end of the elongate body, wherein a distalmost edge of the elongate push member contacts a proximal end of the reinforcement member, and wherein a portion of the elongate push member is positioned between the inner liner and the outer jacket.

\* \* \* \* \*